US007112723B2

(12) United States Patent
Streatfield et al.

(10) Patent No.: US 7,112,723 B2
(45) Date of Patent: Sep. 26, 2006

(54) GLOBULIN 2 REGULATORY REGION AND METHOD OF USING SAME

(75) Inventors: Stephen Streatfield, Bryan, TX (US); Robert Love, Bryan, TX (US); Jeff Bray, Bryan, TX (US)

(73) Assignee: Applied Biotechnology Institute, San Luis Obispo, CA (US)

( * ) Notice: Subject to any disclaimer, the term of this patent is extended or adjusted under 35 U.S.C. 154(b) by 0 days.

(21) Appl. No.: 11/190,408

(22) Filed: Jul. 27, 2005

(65) Prior Publication Data

US 2006/0026717 A1 Feb. 2, 2006

Related U.S. Application Data

(60) Provisional application No. 60/591,695, filed on Jul. 28, 2004.

(51) Int. Cl.
*C12P 7/62* (2006.01)
*C12P 11/00* (2006.01)
*C07H 21/04* (2006.01)
*A01H 1/00* (2006.01)

(52) U.S. Cl. ..................... 800/295; 435/69.1; 435/468; 435/320.1; 435/410; 435/419; 435/6; 435/183; 530/350; 530/370; 536/23.1; 536/23.2; 536/23.6; 536/24.1; 800/278; 800/281; 800/284; 800/287

(58) Field of Classification Search ................ 800/295, 800/278, 370, 287; 435/69.1, 71.1, 91.4, 435/419; 536/23.6, 410, 23.2, 24.1
See application file for complete search history.

(56) References Cited

U.S. PATENT DOCUMENTS 5,270,200 A 12/1993 Sun ............................ 800/302
5,559,223 A 9/1996 Falco ......................... 800/278
5,795,735 A 8/1998 Lockerbie .................. 435/69.1
5,990,390 A 11/1999 Lundquist ................... 800/302
5,994,304 A 11/1999 Lockerbie .................... 514/12
6,025,545 A 2/2000 Lundquist ................ 800/300.1

FOREIGN PATENT DOCUMENTS

WO WO 91/19801 12/1991
WO WO 01/16307 3/2001

OTHER PUBLICATIONS

Lai, et al GenEmbl Databse, Accession No. AC152918.*
Wallace et al. (1991) "Nucleotide sequence of a cDNA clone corresponding to the maize globulin-2 gene" Plant Physiol. 95:973-975.
Kriz et al.(1989) "Characterization of embryo globulins encoded by the maize GIb genes" Biochem. Genet. 27 (3/4):239-257.
Kriz et al. (1991) "Characterization of the maize globulin-2 gene and analysis of two null alleles" Biochem. Genet. 29 (5/6): 241-254.
Hood et al. (2003) Plant Biotechnology Journal 1:129-140.
Woodard et al. (2003) Biotech Appl. Biochem. 38:123-130.

(Continued)

*Primary Examiner*—Phuong T. Bui
*Assistant Examiner*—Brendan O. Baggot
(74) *Attorney, Agent, or Firm*—Patricia A. Sweeney

(57) ABSTRACT

A globulin-2 regulatory region is shown, which provides improved seed preferred, and particularly embryo preferred expression in plants. Methods of use are also shown in preferentially expressing a heterologous protein to the embryo tissue of a plant. The sequence is particularly useful in expression of heterologous proteins to the embryo of monocotyledonous plants, particularly cereals, and maize.

11 Claims, 7 Drawing Sheets atggtccgtcctgtagaaaccccaacccgtgaaatcaaaaaactcgacggcctgtgggcattcagtctggatcgcgaaaactgt
ggaattgatcagcgttggtgggaaagcgcgttacaagaaagccgggcaattgctgtgccaggcagttttaacgatcagttcgcc
gatgcagatattcgtaattatgcgggcaacgtctggtatcagcgcgaagtctttataccgaaaggttgggcaggccagcgtatcgt
gctgcgtttcgatgcggtcactcattacggcaaagtgtgggtcaataatcaggaagtgatggagcatcagggcggctatacgcc
atttgaagccgatgtcacgccgtatgttattgccgggaaaagtgtacgtatcaccgtttgtgtgaacaacgaactgaactggcaga
ctatcccgccgggaatggtgattaccgacgaaaacggcaagaaaaagcagtcttacttccatgatttctttaactatgccggaatc
catcgcagcgtaatgctctacaccacgccgaacacctgggtggacgatatcaccgtggtgacgcatgtcgcgcaagactgtaa
ccacgcgtctgttgactgccaggtggtggccaatggtgatgtcagcgttgaactgcgtgatgcggatcaacaggtggttgcaact
ggacaaggcactagcgggactttgcaagtggtgaatccgcacctctgccaaccgggtgaaggttatctctatgaactgtgcgtca
cagccaaaagccagacagagtgtgatatctacccgcttcgcgtcggcatccggtcagtggcagtgaagggccaacagttcctg
attaaccacaaaccgttctactttactggctttggtcgtcatgaagatgcggacttacgtggcaaaggattcgataacgtgctgatg
gtgcacgaccacgcattaatggactggattggggccaactcctaccgtacctcgcattacccttacgctgaagagatgctcgact
gggcagatgaacatggcatcgtggtgattgatgaaactgctgctgtcggctttaacctctctttaggcattggtttcgaagcgggca
acaagccgaaagaactgtacagcgaagaggcagtcaacggggaaactcagcaagcgcacttacaggcgattaaagagctga
tagcgcgtgacaaaaaccacccaagcgtggtgatgtggagtattgccaacgaaccggatacccgtccgcaagtgcacgggaa
tatttcgccactggcggaagcaacgcgtaaactcgacccgacgcgtccgatcacctgcgtcaatgtaatgttctgcgacgctcac
accgataccatcagcgatctctttgatgtgctgtgcctgaaccgttattacggatggtatgtccaaagcggcgatttggaaacggc
agagaaggtactggaaaaagaacttctggcctggcaggagaaactgcatcagccgattatcatcaccgaatacggcgtggata
cgttagccgggctgcactcaatgtacaccgacatgtggagtgaagagtatcagtgtgcatggctggatatgtatcaccgcgtcttt
gatcgcgtcagcgccgtcgtcggtgaacaggtatggaatttcgccgattttgcgacctcgcaaggcatattgcgcgttggcggta
acaagaaagggatcttcactcgcgaccgcaaaccgaagtcggcggcttttctgctgcaaaaacgctggactggcatgaacttcg
gtgaaaaaccgcagcagggaggcaaacaacaccatcaccatcaccat

OTHER PUBLICATIONS

GenBank accession No. 21213157/ AY109436; Zea mays CL1124_1 mRNA sequence 2002.

GenBank accession No. 26986203/ X53715; Z. mays mRNA for globulin-2 1990.

GenBank accession No. 18568234/AF466203; Zea mays clone ZMBBb_0092E12, partial sequence 2002.

GenBank accession No. 22185/ X70153 Z. mays mRNA for b-32 protein, putative regulatory factor of zein expression (clone b-32. 120) 1990.

GenBank accession No. 22187/X54212; Z. mays mRNA for b-32 protein, putative regulatory factor of zein expression (clone b-32-129) 1990.

* cited by examiner

Figure 1A atggtccgtcctgtagaaaccccaacccgtgaaatcaaaaaactcgacggcctgtgggcattcagtctggatcgcgaaaactgt
ggaattgatcagcgttggtgggaaagcgcgttacaagaaagccgggcaattgctgtgccaggcagttttaacgatcagttcgcc
gatgcagatattcgtaattatgcgggcaacgtctggtatcagcgcgaagtctttataccgaaaggttgggcaggccagcgtatcgt
gctgcgtttcgatgcggtcactcattacggcaaagtgtgggtcaataatcaggaagtgatggagcatcagggcggctatacgcc
atttgaagccgatgtcacgccgtatgttattgccgggaaaagtgtacgtatcaccgtttgtgtgaacaacgaactgaactggcaga
ctatcccgccgggaatggtgattaccgacgaaaacggcaagaaaaagcagtcttacttccatgatttctttaactatgccggaatc
catcgcagcgtaatgctctacaccacgccgaacacctgggtggacgatatcaccgtggtgacgcatgtcgcgcaagactgtaa
ccacgcgtctgttgactgccaggtggtggccaatggtgatgtcagcgttgaactgcgtgatgcggatcaacaggtggttgcaact
ggacaaggcactagcgggactttgcaagtggtgaatccgcacctctgccaaccgggtgaaggttatctctatgaactgtgcgtca
cagccaaaagccagacagagtgtgatatctacccgcttcgcgtcggcatccggtcagtggcagtgaagggccaacagttcctg
attaaccacaaaccgttctactttactggctttggtcgtcatgaagatgcggacttacgtggcaaaggattcgataacgtgctgatg
gtgcacgaccacgcattaatggactggattggggccaactcctaccgtacctcgcattacccttacgctgaagagatgctcgact
gggcagatgaacatggcatcgtggtgattgatgaaactgctgctgtcggctttaacctctctttaggcattggtttcgaagcgggca
acaagccgaaagaactgtacagcgaagaggcagtcaacggggaaactcagcaagcgcacttacaggcgattaaagagctga
tagcgcgtgacaaaaaccacccaagcgtggtgatgtggagtattgccaacgaaccggatacccgtccgcaagtgcacgggaa
tatttcgccactggcggaagcaacgcgtaaactcgacccgacgcgtccgatcacctgcgtcaatgtaatgttctgcgacgctcac
accgataccatcagcgatctctttgatgtgctgtgcctgaaccgttattacggatggtatgtccaaagcggcgatttggaaacggc
agagaaggtactggaaaaagaacttctggcctggcaggagaaactgcatcagccgattatcatcaccgaatacggcgtggata
cgttagccgggctgcactcaatgtacaccgacatgtggagtgaagagtatcagtgtgcatggctggatatgtatcaccgcgtcttt
gatcgcgtcagcgccgtcgtcggtgaacaggtatggaatttcgccgattttgcgacctcgcaaggcatattgcgcgttggcggta
acaagaaagggatcttcactcgcgaccgcaaaccgaagtcggcggcttttctgctgcaaaaacgctggactggcatgaacttcg
gtgaaaaaccgcagcagggaggcaaacaacaccatcaccatcaccat

Figure 3 gcgatctgaagatctggtgaacctgagcctgacccatcaaatgtctataagttttctttgtagagaaattatcggctccccaaatgag
tttccaagcatcatttgtattggccaccatgatttggccccaagttgcgtctaagtctagaaattgttcataagcttgcaccgacaga
ggtagctgaaaaatttcaataagttgttccttttggagagcttctttgatggtaagtttgctgttgcaagcaaaggaaaataactcagg
atattgatgagccgggatgcccctattccacatatcttcccagaaaagaatggttcttccatccccgatagttggggcagccagtc
ccttgtaatcttggacaagagtaagcaagcttttccaccaaaaggagccaatttttgagcaaccaggtagcctgactgtcctgtaat
agttgctccaaaccaggttaacccagggaatatcatgattgttgaaaaacttgtgcaaaaacttcagaagcaaggctttattgtgag
tctctaatcttaccactcccaggcccccatttttttagtctgtgtaatcatactccaagtagctagagcaggtttctttgaattgacgtcg
tttcctctccaaagacagtgtttccgataagaatcaatcttctttaccgtggtaaccggaattttcagtgtgcacatcaaaaaggtcgg
gagagctgagaacaccgagttaacaagctcaagcctgccagcctgggagaggagggcagaggtgcatgataatctcttttgaa
tcctatgaatgagcggtaaaaagtggcagattttaggctttgatagaccaagcggaacaccaagataggtaaagggcattgaac
ctatctgacagttgagggttcctgctaggatcgccattttagcaggactgacattgatggggtacatacttgatttgttgtaattcacc
ttcaaccccgtcgaagttgcaaaagagttcagaacggctctgagaaaaaatagctgtctagggcaagcttccattatcagtagtgt
gtcatccgcatattgaactatcggaaaatcttgaccacaattctcggccaggggtaacttgagaaggtcttgctgccgcgctttatt
gatgatgctctgtaacagatccgccgcgagaacaaaaagaagaggcgagaggggatctccctgcctaaccccacgcttgtagt
gaaaggttttcccaggaacaccattaagaaggactgatgacgtgctagaccgaagaatatccctaatccagctcatccatctggg
cccaaagcctctatgcaacattacctgaagaatcaactcatgctcaagagaatcaaaagccttttcaaaatccaatttgagcacaat
aatctctttttttgaaatatgacaaagatgaatatattcaaatgcccaggccagacaatcctgaatggttctttctttgatgaagccata
ttgatttttgtgaacaagggaagtcatcactgtctgtaaccggttagccagcagcttagtgatgattttcatactattattcagaagcg
aaattggtctgaaatcgcccactaaactagcattatccttcttcggaatcaggacaatataagaaccattgatgcttcgaagacaaa
tatccccgtggtaaaattggtcacataagtcatagaagtcctgggaaataatcggacaacatttttttgataaagttggtattaaaccc
atcaggtcccggggatttatcagaaggaagggacgccacaatactatcaatttcttgctttgaaaaaggctcatctaaccaatgca
agtcattgcggcagagcaacaaactagaaagatcaaagacattatccacaaaatcggaggatcccaagcgacatttgaacatatt
ccaaagcaggttagttttgagatcatgctctgtaaagattgagccactgtcatccaagagcaacgcaattgtattacggccatgcc
acgcaactgtcatccaagaactttctactcttggattacacggataaagttgaagtactacaagcaactataaacgactagagcctt
tgcttgagtccttttatacgcggtcgaagagtgtttgcctctttatttatttgttcagcaggccccgagaatcttcaccgctgaagcac
acccgacccgaataattgataatattgctcaaatcatatgagatggacgctggctctgcagcttttagggcctgttcgtttgactcgg
aattcatcccggaattgttccagctaatcaaatgttatataaattagataaccaatccggctaggaatagttccggacggccaattcc
tcagaatcgaacgggcccttagctagtttcgagtcgtcggaatcagcttctgctagctaaatgttttgcttttcatagtctatttttgtta
gaatcgtttatataaaaattacatctaaatatagaatctatcgaatcgtcgtgatagtatgaatgtgatgctgcgcgtagactcctttgt
cttctttagcacataaatcgtataaaaattgtcgtaacagctattttttaagaatccagattatcagaaatctttgggaaaaaaagcact
ctctgaaaaagccccgcgtcgctacgtgcagctccatctgctccgtgttgtccccatcccaatcaccgctgtcgcttcgccgcag
gcatcccagcagcgagctagcatgcacgcacgcacgcaagcacacggcggcagctgcacggatgcggccgagtgcggtag
cactgcagcgcgcgcgcgcgctccacatcgccttcgccccgccacgtacgcggcccggcctccacctggcggcgcgcatgg
ctgcgaccctcgccgcgccacctcttcatatacgccgcagctcgcttcgaaccctcgcatcgaacgcacactcgcactcgcagt
cgcacgtacacggtacaccacactagctaccacagacgacgagcgccATG

GLOBULIN 2 REGULATORY REGION AND METHOD OF USING SAME

REFERENCE TO RELATED APPLICATIONS

This application claims benefit under 35 U.S.C. § 119(e) to previously filed and co-pending application U.S. Ser. No. 60/591,695, filed Jul. 28, 2004, the contents of which are incorporated in their entirety.

BACKGROUND OF THE INVENTION

Promoters are vital molecular tools that have been applied widely in plant biotechnology to control the expression of introduced genes. There are many applications for promoters in driving gene expression in plant tissues. These include the synthesis of scoreable and selectable markers to identify transgenic plants (Jefferson et al., 1987; Wohlleben et al., 1988) and the over-expression of control point enzymes to modify metabolic flux through key pathways, so affecting the yields of important plant products (Nessler, 1994; Lessard et al., 2002). Other uses of plant promoters include the expression of genes conferring resistance to pests, thus conferring protection (Estruch et al., 1997), and the expression of non-native enzymes to facilitate the production of foreign metabolites in particular plant species (Poirier et al., 1995; Ye et al., 2000). A further application of plant promoters is to over-express controlling regulatory genes affecting aspects of plant physiology such as flowering time and so modify plant growth characteristics (Weigel and Nilsson, 1995). Promoters are also used to repress the expression of specific genes by driving the synthesis of interfering RNA species (Waterhouse et al., 2001), thus affecting plant metabolic and developmental pathways (Yu and Kumar, 2003). Although high levels of expression may not be necessary for all of the above applications, there is clearly a need for promoters showing activity in plant tissues.

Apart from these and other applications of promoters to modify plant traits, promoters are also required for plants to act as production systems for heterologous proteins. Plants have been used to produce a wide range of recombinant proteins of potential economic and/or medicinal importance. These include research chemicals (Hood et al., 1997; Zhong et al., 1999), processing enzymes that are used, for example, in the pharmaceutical industry (Woodard et al., 2003), industrial enzymes that are deployed in large-scale processing operations such as bleaching (Hood et al., 2003; Bailey et al., 2004), candidate vaccine antigens for animal or plant disease prevention (Mason et al., 1992; Haq et al., 1995; Carrillo et al., 1998; Streatfield et al., 2001), and therapeutic pharmaceuticals including antibodies (Daniell et al., 2001; Hood et al., 2002). The expressed proteins may either be purified from the plant tissues (Hood et al., 1997; Woodard et al., 2003) or, if as with vaccines the final application allows it, the recombinant plant material may be processed into a suitable form for use or even deployed directly (Streatfield et al., 2002; Lamphear et al., 2002). For these and other protein products to be produced in plant systems it is necessary that promoters drive a sufficiently high level of expression to ensure commercial viability.

Spatial and temporal control is also often important in driving gene expression in plants. For example, selectable and scoreable markers must be expressed at a suitable time and in an appropriate tissue to allow for screening, and controlling enzymes and regulatory factors must be produced in metabolically active and physiologically responsive tissues, respectively. Similarly, genes conferring host protection must be expressed in the target tissues for the pathogen or pest, and plant produced protein products should be expressed in tissues suitable for protein accumulation and storage. Furthermore, since certain protein products may have detrimental affects on plant health and yield when expressed in metabolically active plant tissues that are essential for survival and growth, promoters may be favored that are active in the chosen plant storage tissues but show low or no activity in other, non-storage tissues.

Promoters that preferentially express relatively high levels of foreign proteins in tissues suitable for stable protein accumulation and storage are particularly useful for commercial protein production. The seed tissues of the cereals are especially well suited to the large-scale production of recombinant proteins. Thus, there is a requirement for promoters that show a seed tissue preferred expression pattern in plants and particularly cereals and drive relatively high levels of protein accumulation in these tissues.

Several promoters of plant and plant pathogen (bacterial and viral) origin have been used to direct transgene expression in plants. Prominent examples include the French bean beta-phaseolin promoter (Bustos et al., 1989), the mannopine synthase promoter of *Agrobacterium tumefaciens* (Leung et al., 1991), and the 35S promoter of cauliflower mosaic virus (Guilley et al., 1982). These and several other promoters in widespread use in plants were originally developed and utilized in dicot species. Promoter sequences from one species are predictably used in other species (see discussion below). The cereals comprise particularly important crops and there is therefore a pressing need for promoters that have high activity and/or tissue preference in monocots. Cereals, such as grasses, are cultivated for their grain. Since the nutritional value of cereals is in their seeds, and these tissues are also well suited for recombinant protein accumulation and storage, promoters that are active in cereal seed tissues are especially useful.

Two broad classes of promoters are typically deployed: constitutive and tissue preferred. Constitutive promoters, such as maize polyubiquitin-1 drive expression in the seed but also in other tissues (Christensen et al., 1992). A drawback with such constitutive promoters is that expression in tissues other than seed storage tissues may result in plant health being compromised, for example if a potentially toxic protein is expressed in metabolically active tissues required for germination or growth (Hood et al., 2003). Furthermore, constitutive expression may result in the expressed foreign protein being synthesized in pollen grains and thus being difficult to contain. By contrast, seed preferred promoters limit all or the bulk of transgene expression to seed tissues, so avoiding such concerns. Tissue preferred expression can include seed preferred expression. An example of one such promoter providing seed preferred expression is the phaseolin promoter. See, Bustos et al. "Regulation of β-glucuronidase Expression in Transgenic Tobacco Plants by an A/T-Rich cis-Acting Sequence Found Upstream of a French Bean β-Phaseolin Gene" *The Plant Cell Vol.* 1, 839–853 (1989).

The principle tissue types in maize seeds are the embryo, the endosperm including a surrounding aleurone cell layer and the maternally derived pericarp. Of these, the endosperm and to a lesser extent the embryo, comprise most of the volume of the seed. Thus, endosperm and embryo promoters are particularly important for modifying seed characteristics and contents. The proximal 1.1 kb of a maize 27 kD γ-zein promoter (Russell and Fromm, 1997) and the proximal 1.45 kb of a maize globulin-1 promoter (Belanger and Kriz, 1991; Genbank accession L22344) are prominent examples of seed preferred promoters that have been used to express transgenes in the seeds of monocots.

The endosperm is comprised almost entirely of nutritional reserves, primarily of complex carbohydrate and insoluble protein, but the embryo also contains considerable stores, mainly of oils and soluble proteins. Globulin-1 is one of the most abundant proteins in maize embryo tissue. It is largely limited to this tissue and becomes particularly concentrated in the scutellum late in embryo development. Given the high concentration of this protein observed in embryo tissues a maize globulin-1 promoter was identified as being a good candidate to direct high levels of transgene expression in the embryo. An approximately 1.45 kb extent of a maize globulin-1 promoter/leader has been cloned (Belanger and Kriz, 1991; Genbank accession L22344) and used to drive high levels of transgene expression preferentially in maize seeds (Hood et al., 2003; Woodard et al., 2003). However, still more active promoters are very desirable for some applications, such as the expression of cost sensitive foreign proteins in cereal seeds.

However, despite these examples, there is currently a very limited repertoire of promoters for preferentially expressing foreign proteins in the seed tissues of plants, and in particular, cereals. There is a need for further promoters that express transgenes at similar or higher levels to those currently deployed and with similar or improved tissue specificity. The best promoters would facilitate the expression of foreign proteins in seeds at higher levels than are currently achieved, while restricting expression specifically or predominantly to seed tissues. Also, a range of new promoters would allow the expression of multiple copies of a single transgene in seeds without the need to repeatedly use the same promoter. This should reduce silencing phenomena associated with promoter methylation (De Wilde et al., 2000), and thereby it should also serve to boost expression. Similarly, multiple distinct transgenes could be simultaneously expressed from different promoters in seed tissues, allowing more complex traits and foreign protein products to be reliably introduced into seeds.

All references cited herein are incorporated herein by reference.

SUMMARY OF THE INVENTION

A *Zea mays* globulin-2 regulatory region has been identified and has preferential expression to the embryo of a plant. It has been found to drive one of the most prevalent messages in developing maize embryos. This invention describes a sequence proximal to a maize globulin-2 gene with improved preferential transgene expression in plant embryo tissues. In an embodiment, it is used to drive expression preferentially to embryos in monocotyledonous plants, particularly cereal plants, and most preferentially, in maize.

DESCRIPTION OF THE DRAWINGS

FIG. 1A shows the nucleotide sequence (SEQ ID NO: 1) and FIG. 1B shows the encoded amino acid sequence (SEQ ID NO: 2) of the β-glucuronidase gene used in experiments.

FIG. 3 shows the nucleotide sequence of the proximal approximately 3 kb of DNA upstream of the here cloned maize globulin-2 translation start codon. The untranslated leader sequence is given in bold type and the translation start codon is capitalized. The entire sequence is SEQ ID NO: 3, the promoter is SEQ ID NO: 4 and the untranslated leader sequence is SEQ ID NO: 5.

DESCRIPTION OF THE PREFERRED EMBODIMENTS

Figure 2A:
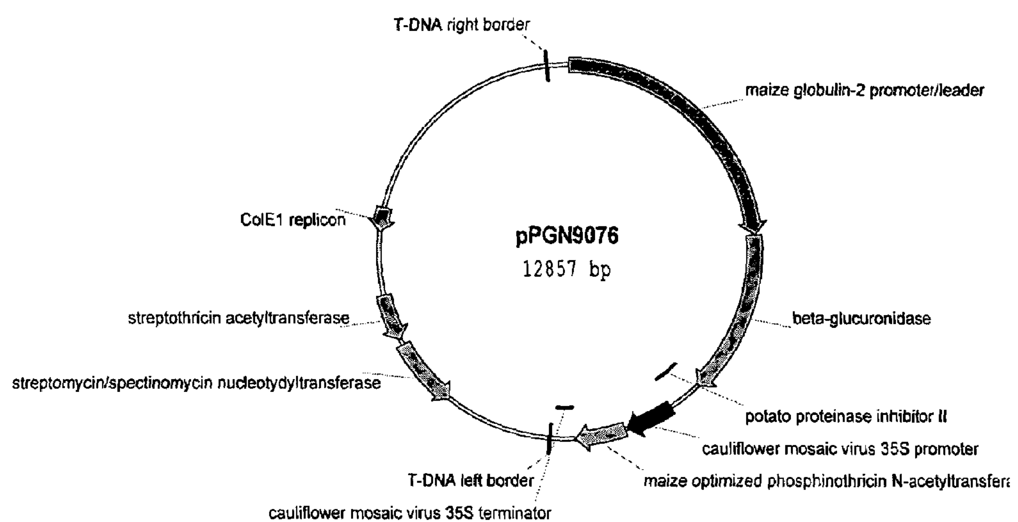
FIG. 2 shows vector maps of reporter constructs with FIG. 2A showing pPGN9076 (globulin-2 promoter/leader fused to uidA)
FIG. 2B shows pPGN9078 (globulin-2 promoter/leader fused to maize codon optimized and cell surface targeted aprotinin).

Nucleotide sequences are described herein that regulate transcription with preferential expression to plant seed tissue, and preferential expression to plant embryo tissue in the seed. These novel nucleotide sequences are those natively associated with the nucleotide sequence coding for *Zea mays* globulin-2 and comprise SEQ ID NO: 3.

A genomics approach can be used and is described to identify further sequences that can drive high levels of transgene expression in maize embryo tissues. The sequence is shown in FIG. 3. It includes the sequences up to but not including the translation start site, ATG. This is SEQ ID NO: 3 and includes the proximal approximately 3 kb of a maize globulin-2 promoter (SEQ ID NO: 4) plus untranslated leader (SEQ ID NO: 5), also referred to as the "here cloned" promoter or regulatory region). Transgenic plants generated using this sequence show similar expression to those generated using a previously cloned approximately 1.45 kb maize globulin-1 promoter plus untranslated leader (Belanger and Kriz, 1991; Genbank accession L22344), which has previously been deployed to express transgenes in maize seeds (Hood et al., 2003; Woodard et al., 2003). Furthermore, this new globulin-2 promoter plus untranslated leader sequence cloned here is highly embryo preferred in its expression pattern, as is the previously cloned globulin-1 promoter sequence. Thus, this new maize globulin-2 promoter plus untranslated leader sequence cloned here is well suited to drive transgene expression in maize and other plant seeds. The here cloned promoter is particularly useful for the expression of gene sequences in cereal plants and especially in maize plants. However, it can be used in any plant species, including, for example, a monocotyledonous plant such as wheat, rye, rice, oat, barley, turfgrass, sorghum, millet or sugarcane. Alternatively, the plant may be a dicotyledonous plant, for example, tobacco, tomato, potato, soybean, cotton, canola, sunflower or alfalfa. Maize promoters have been used repeatedly to drive expression of genes in non-maize plants, including tobacco (Yang and Russell, 1990; Geffers et al., 2000; Vilardell et al., 1991), cultured rice cells (Vilardell et al., 1991), wheat (Oldach et al., 2001; Brinch-Pedersen et al., 2003), rice (Cornejo et al., 1993; Takimoto et al., 1994), sunflower (Roussell et al., 1988) and protoplasts of carrot (Roussell et al., 1988).

The nucleotide sequences of the invention can be used to isolate corresponding sequences from other organisms, particularly other plants, more particularly other monocots, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of the maize globulin-2 promoter and untranslated leader sequences set forth herein are encompassed by the present invention. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989; Innis et al., 1990; Innis et al., 1995; Innis et al., 1999). Known methods of PCR include, but are not limited to, methods using paired primers, nested primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the globulin-2 promoter and untranslated leader sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m$=81.5° C.+16.6 (logM)+0.41(% GC)−0.61(% form.)−500/L, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993) and Sambrook et al. (1989).

Thus, isolated sequences that have promoter activity and which hybridize under stringent conditions to the promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988), the local homology algorithm of Smith and Waterman (1981), the homology alignment algorithm of Needleman and Wunsch (1970), the search-for-similarity-method of Pearson and Lipman (1988) and the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif., USA); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins and Sharp (1988), Higgins and Sharp (1989), Corpet (1988), Huang et al. (1992) and Pearson (1994). The ALIGN program is based on the algorithm of Myers and Miller (1988). The BLAST programs of Altschul et al. (1990) are based on the algorithm of Karlin and Altschul (1990). To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules, see Altschul et al. (1997). When utilizing BLAST, Gapped BLAST or PSI-BLAST, the default parameters of the respective programs (e.g. BLASTN for nucleotide sequences, BLASTX for proteins) can be used, see the World Wide Web site ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an identical or similar alignment of nucleotide matches and percent sequence identity when compared to the corresponding alignment generated by the preferred program.

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The invention is further to "functional variants" of the regulatory sequence disclosed. Functional variants include, for example, regulatory sequences of the invention having one or more nucleotide substitutions, deletions or insertions and wherein the variant retains promoter activity, particularly the ability to drive expression preferentially to the embryo of a plant. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis, or similar techniques. The '484 patent describes the identification of functional variants of different promoters.

The promoter of the invention may be combined with any number of other components to be introduced into the plant, including combined with a gene of interest to be expressed in the plant. The "gene of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets an area of the chromosome in the plant but may not encode a protein. If desired, the gene of interest can be optimized for plant translation by optimizing the codons used for plants and the sequence around the translational start site for plants. Sequences resulting in potential mRNA instability can also be avoided.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. By "seed preferred" is intended favored expression in the seed of the plant, and "embryo preferred" indicates favored expression in the embryo of the seed of the plant.

The promoter of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet third and fourth embodiments, the expression vector can contain two or more genes of interest that can be linked to the same promoter or different promoters. For example, the globulin-2 promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (European patent application no. 0 342 926); the promoter for the small subunit of ribulose-1,5-bis-phosphate carboxylase (ss-RUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed in the present invention.

A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the embryo can be identified, isolated, and used with other core promoters to confirm embryo-preferred expression. By core promoter is meant the sequence sometimes referred to as the TATA box (or similar sequence) which is common to promoters in most genes encoding proteins. Thus the upstream promoter of extended globulin-2 can optionally be used in conjunction with its own or core promoters from other sources In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989).

One skilled in the art readily appreciates that the promoter can be used with any of a variety of nucleotide sequences comprising the gene of interest to be expressed in plants. For example, the gene of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

The gene of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the promoter can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

Clearly, many variations in use of the promoter of the invention are available to one skilled in the art.

In one embodiment, the expression vector also contains a gene encoding a selectable or scoreable marker that is operably or functionally linked to a promoter that controls transcription initiation, which can be the promoter of the invention or another promoter. By “operably linked” it is understood that the gene of interest (in this case the gene encoding a selectable or scoreable marker) is oriented in connection to the promoter such that the promoter initiates transcription of the gene in order to allow its expression of the resulting protein in plants. For a general description of plant expression vectors and reporter genes, see Gruber et al. (1993). In one embodiment, the selective gene is a glufosinate-resistance encoding DNA and in another embodiment it can be phosphinothricin acetyl transferase (pat) or a maize optimized pat gene under the control of the CaMV 35S promoter. Such pat genes confer resistance to the herbicide bialaphos (Gordon-Kamm et al., 1990).

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley α-amylase secretion signal (Rogers, 1985). Many signal sequences are known in the art. See, for example Becker et al. (1992), Fontes et al. (1991), Matsuoka and Nakamura (1991), Gould et al. (1989), Creissen et al. (1992), Kalderon et al. (1984) and Stiefel et al. (1990).

Leader sequences can be included to enhance translation. Instead of, or in addition to the untranslated leader sequence of the globulin-2 promoter, other leader sequences may be substituted or added. Translation leaders are known in the art and include: picomavirus leaders, for example, EMCV leader (Encephalomyocarditis 5' noncoding region) (Elroy-Stein et al. (1989); potyvirus leaders, for example, TEV leader (Tobacco Etch Virus) (Gallie et al. (1995)); human immunoglobulin heavy-chain binding protein (BiP) (Macejak et al. (1991)); untranslated leader from the coat protein mRNA of alfalfa mosaic virus (AMV RNA 4) (Jobling et al. (1987)); tobacco mosaic virus leader (TMV) (Gallie. (1989)); and maize chlorotic mottle virus leader (MCMV) (Lommel et al. (1991)). See also, Della-Cioppa et al. (1987). Other methods known to enhance translation can also be utilized, for example, introns, and the like. Obviously, many variations on the promoters, selectable markers, signal sequences, leader sequences, termination sequences, introns, enhancers and other components of the construct are available to one skilled in the art.

Methods for introducing expression vectors into plant tissue available to one skilled in the art are varied and will depend on the plant selected. Procedures for transforming a wide variety of plant species are well known and described throughout the literature. See, for example, Miki and McHugh (2004); Klein et al. (1992); and Weising et al. (1988). For example, the DNA construct may be introduced into the genomic DNA of the plant cell using techniques such as microprojectile-mediated delivery (Klein et al. 1992), electroporation (Fromm et al., 1985), polyethylene glycol (PEG) precipitation (Mathur and Koncz, 1998), direct gene transfer (WO 85/01856 and EP-A-275 069), in vitro protoplast transformation (U.S. Pat. No. 4,684,611) and microinjection of plant cell protoplasts or embryogenic callus (Crossway, 1985). Co-cultivation of plant tissue with *Agrobacterium tumefaciens* is another option, where the DNA constructs are placed into a binary vector system (Ishida et al., 1996). The virulence functions of the *Agrobacterium tumefaciens* host will direct the insertion of the construct into the plant cell DNA when the cell is infected by the bacteria. See, for example, Fraley et al. (1983).

Standard methods for transformation of canola are described by Moloney et al. (1989). Corn transformation is described by Fromm et al. (1990) and Gordon-Kamm et al. (1990). *Agrobacterium* is primarily used in dicots, but certain monocots such as maize can be transformed by *Agrobacterium*. See, for example, U.S. Pat. No. 5,550,318. Rice transformation is described by Hiei et al. (1994) and Lee et al. (1991). Wheat can be transformed by techniques similar to those used for transforming corn or rice. Sorghum transformation is described by Casas et al. (1993) and barley transformation is described by Wan and Lemaux (1994). Soybean transformation is described in a number of publications, including U.S. Pat. No. 5,015,580.

In one preferred method, the *Agrobacterium* transformation methods of Ishida et al. (1996) and also described in U.S. Pat. No. 5,591,616, are generally followed, with modifications that the inventors have found improve the number of transformants obtained. The Ishida method uses the A1188 variety of maize that produces Type I callus in culture. In one preferred embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in the U.S. Pat. No. 5,591,616, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in the U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600}$=0.5, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

In accordance with the present invention, a transgenic plant is produced that contains an introduced globulin-2 promoter. It can be combined with any one of the components set forth above. In a preferred embodiment, the promoter is driving expression of a nucleotide sequence such that the sequence encodes a protein preferentially expressed in the seed of the plant. Preferably, the plant is a cereal plant, and most preferably, a maize plant.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman and Sleper (1995). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

EXAMPLES

The following is presented as illustrative of an embodiment of the invention and does not limit the scope of the invention as otherwise set forth.

Materials and Methods

Construction of cDNA Libraries Representative of Maize Embryo Tissues

Maize plants were grown from seed in moist soil under standard greenhouse conditions. Four lines of maize were grown, representative Lancaster, Stiff Stalk, high protein and high oil lines. Elite inbreds are commonly derived from germplasm pools known as Stiff Stalk and Lancaster. Stiff Stalk inbreds have been known for decades and are reported by the USDA to have been widely available for decades. They are derived from the Iowa Stiff Stalk synthetic population (Sprague, 1946). For example see PI accession no. 550481 and discussions of Stiff Stalk germplasm at U.S. Pat. Nos. 5,706,603; 6,252,148; 6,245,975; 6,344,599 and 5,134,074. See also, Neuhausen (1989). Lancaster inbreds are derived from the open pollinated variety Lancaster Surecrop (Anderson, 1944). See for example, PI 280061. High oil or high protein plants are those in which the oil or protein content of the seed is higher than lower oil or protein producing plants such as hybrid #2 yellow dent corn.

Plants were self-pollinated and individual plants were sacrificed at 10, 11, 12, 19, 28, 37 and 46 days post-pollination. Embryos were immediately harvested from these plants, frozen in liquid nitrogen and stored at −80° C. Embryos harvested from distinct lines and at different time points were kept separate, except that embryos of the same line harvested at 10, 11 and 12 days post-pollination were pooled. For each of the five resulting time points (10 to 12 days, 19 days, 28 days, 37 days and 46 days post-pollination) equal amounts of embryo tissues harvested from each of the four maize lines were pooled. Total RNA was isolated from the pooled embryo tissues using a phenol-based method (Chatterjee et al., 1996), and poly-A message was then prepared from this RNA using Poly(A) Quik mRNA isolation columns (Stratagene; La Jolla, Calif.). These poly-A RNA samples were used to prepare five cDNA libraries, each representative of all four maize lines and each corresponding to a different time point of embryo development. The libraries were constructed in the Lambda ZAP II vector (Stratagene; La Jolla, Calif.).

DNA Sequence Analysis of Representative Clones from Maize Embryo Libraries

For each of the five libraries, phagemids were excised from the phage vector. Approximately 100 clones were randomly selected to represent each library and the nucleotide sequences of the cDNA inserts were determined using the chain termination approach using attached dyes by the 'DNA Sequencing and Synthesis Facility' of Iowa State University (Ames, Iowa). Nucleotide sequences of clones were compared using the 'Sequencher' package (Gene Codes Corporation; Ann Arbor, Mich.).

Analysis of Clone Representation in a Developing Embryo Library by Plaque Hybridization Phage of an equal mixture of each of the five post-pollination embryo cDNA library time points was infected onto the bacterial strain XL1-Blue MRF' (Stratagene; La Jolla, Calif.) to generate approximately 80,000 plaques upon plating. Phage DNA was transferred onto charged nylon filters (Amersham; Piscataway, N.J.) and cross-linked to the filters by exposure to ultraviolet light. Radionucleotide ($^{32}P$) was incorporated into globulin-2 cDNA sequence by random prime labeling (Feinberg and Vogelstein, 1983) using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.), to reveal clones homologous to globulin-2 cDNA.

Analysis of Genome Organization by DNA Hybridization

DNA was prepared from maize leaves using a hexadecyltrimethyl-ammonium bromide based method (Stacey and Issac, 1994). DNA (15 μg samples) was digested with the restriction endonucleases EcoRI or HindIII and DNA fragments were size separated on 0.7% agarose gels. Vector DNA was similarly digested and 60 pg was size separated on the gels. The DNA was transferred onto charged nylon filters (Amersham; Piscataway, N.J.) and cross-linked to the filters by exposure to ultraviolet light. Radionucleotide ($^{32}P$) was incorporated into globulin-2 cDNA sequence by random prime labeling using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.).

Analysis of Message Levels by RNA Hybridization

Total RNA was isolated from maize tissues using a phenol-based method (Chatterjee et al., 1996). RNA (20 μg samples) was size separated on agarose/formaldehyde gels, transferred onto charged nylon filters (Amersham; Piscataway, N.J.) and cross-linked to the filters by exposure to ultraviolet light. Radionucleotide labeled DNA probes were prepared by random prime labeling using the 'High Prime' reagent mix (Roche Diagnostics GmbH; Mannheim, Germany) and the filters were incubated with maize globulin-2 cDNA or 18S rRNA gene sequences. Filters were washed under conditions of high stringency (15 mM NaCl, 1.5 mM $Na_3C_6H_5O_7.2H_2O$, 0.1% sodium dodecyl sulfate, 65° C.) and exposed to BioMax MS film (Kodak; Rochester, N.Y.). DNA probes were stripped from filters by washing with near-boiling 0.1% sodium dodecyl sulfate.

Cloning of and Nucleotide Sequence Determination of a Maize Globulin-2 Promoter

DNA sequences upstream of a globulin-2 open reading frame were isolated from a maize Missouri-13 line genomic library in the Lambda FIX II vector (Stratagene; La Jolla, Calif.). The phage library was infected onto the bacterial strain XL1-Blue MRA (Stratagene; La Jolla, Calif.) and plated to generate plaques. Phage DNA was transferred onto charged nylon filters (Amersham; Piscataway, N.J.) and cross-linked to the filters by exposure to ultraviolet light. Radionucleotide ($^{32}P$) was incorporated into globulin-2 cDNA sequence by random prime labeling using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.) to reveal sequences homologous to globulin-2 cDNA. Homologous clones were recovered and the phage inserts mapped by comparing restriction endonuclease digests of the clones following size fractionation via agarose gel electrophoresis. The nucleotide sequence of DNA identified as extending approximately 3 kb 5' of globulin-2 open reading frame sequence was determined by the 'DNA Sequencing Facility' of Iowa State University (Ames, Iowa).

Construction of Promoter-reporter Gene Fusions and Introduction into Plants

The here cloned untranslated leader sequence of globulin-2, plus proximal promoter sequence, together corresponding to approximately 3 kb of sequence 5' to the open reading frame, was fused to the β-glucoronidase (uidA) reporter gene of *Escherichia coli* (Jefferson et al., 1987), and separately to a maize codon optimized sequence encoding the mature chain of the pancreatic trypsin inhibitor aprotinin of *Bos taurus*. (See Greaney, EP 0 587 681; Genbank accession number D38507; Genbank protein sequence accession number P00974). Note that while any version of the uidA gene would be workable in the invention, in this particular instance a version with a six histidine residue (SEQ ID NO: 6) fusion to the C-terminus was used. (See FIG. 1A showing nucleotide sequence used (SEQ ID NO: 1) and FIG. 1B showing the corresponding amino acid sequence (SEQ ID NO:2).) This tag allows for easy isolation from plant tissues using a nickel column, should purification be desired. Where aprotinin was the reporter, DNA encoding the barley alpha-amylase signal sequence was also included immediately upstream of the reporter (Rogers, 1985). To ensure appropriate message termination, the potato proteinase inhibitor II (PinII) transcription terminator region was added 3' of the reporter genes for each fusion (An et al., 1989). These fusions were included on vectors that also carried the phosphinothricin N-acetyltransferase gene (pat) of *Streptomyces viridochromogenes* to confer herbicide resistance to transgenic plants. This gene confers resistance to bialaphos (Gordon-Kamm et al., 1990). The expression of the pat marker was controlled by the cauliflower mosaic virus 35S promoter and terminator sequences (Guilley et al., 1982; Odell et al., 1985). In addition, the vectors contained border sequences flanking the transcription units. These borders allowed the transformation of vector DNA enclosed within them into the target plant's genome. The vectors are shown in FIG. 2.

The procedure for stable transformation was modified from that of Ishida et al. (1996) as described supra. Immature zygotic embryos from kernels of a Hi-II/elite line were transformed with *A. tumefaciens* strain EHA101 containing the relevant globulin-2 upstream sequence/reporter fusions to generate transgenic events. $T_0$ plants were regenerated from tissue culture of each event, transferred to soil in a greenhouse and pollinated using pollen from an elite inbred line to produce $T_1$ seeds.

Quantification of uidA Reporter Gene Expression in Seed Tissues

Six dry seeds from each ear were individually pulverized and extracted with 1 ml of lysis buffer (50 mM sodium phosphate pH 7.0, 1 mM EDTA, 10 mM β-mercaptoethanol). Furthermore, fifty seed pools from each ear were homogenized in a blender and three approximately 100 mg aliquots were extracted with the above lysis buffer. Single and pooled seed samples were placed in extraction tubes held in a rack, with a ball bearing added to each tube, and were then homogenized in a high-speed shaker for 20 seconds. Samples were centrifuged, and the supernatants recovered and stored on ice prior to analysis. Assays were performed in triplicate to determine GUS activity resulting from expression of the uidA reporter gene (Jefferson et al., 1987). Total soluble protein (1 μg) was incubated in 100 μl of lysis buffer and the reaction was initiated with 25 μl of 5 mM 4-methylumbelliferyl β-D-glucuronide (Sigma; St. Louis, Mo.). The reaction was incubated for up to 20 min at 37° C. At specific time points 25 μl volumes of the reaction mixture were transferred to PolySorp 96-well plates (Nalge Nunc International; Rochester, N.Y.) that had 175 μl of stop buffer (0.2M $Na_2CO_3$) per well. Fluorescence was measured at an excitation wavelength of 360 nm and an emission wavelength of 460 nm on a Microplate Fluorometer (Molecular Devices; Sunnyvale, Calif.). GUS protein levels were then calculated by comparison to a standard curve of 1 to 100 μM 4-methylumbelliferone (Sigma; St. Louis, Mo.). Protein concentrations were determined in duplicate using a dye-binding assay (Bradford, 1976).

Statistical Analysis of uidA Reporter Gene Expression in Transgenic Seeds

Following the six individual seed analysis the mean value for all seed expressing above a background cut off level was determined for each plant and separately for the construct. Next, from the mean values for each plant, mean expression levels were determined among all plants derived from a particular independent transformation event and also from all plants derived from the construct. If all seed from a particular plant expressed below the background cut off level, then that plant was scored as zero and was not included in the analysis. Finally, from the mean values for each transformation event, mean levels were determined among all events derived from the construct. If all plants from a particular event had been scored as zero, then that event was scored as zero and was included as such in the analysis.

The single seed data was also analyzed focusing on the highest individual seed for each plant. From the highest individual seed values for each plant, mean of high seed expression levels were determined among all plants derived from a particular independent transformation event and also from all plants derived from the construct. If the highest expressing seed from a particular plant expressed below the background cut off level for the assay, then that plant was scored as zero and was not included in the analysis. Finally, from the mean of high seed values for each transformation event, mean levels were determined among all events derived from the construct. If all plants from a particular event had been scored as zero, then that event was scored as zero and was included as such in the analysis.

The data for the 50 seed pools was similarly analyzed to give mean expression levels for the construct derived from either expression levels determined for each plant's pooled seed or from mean expression levels for each event, which themselves were derived from expression levels for each plant's pooled seed. Note that for the 50 seed pool analysis pooled seed was not assayed from plants that had given no positive seed by the six individual seed analysis. Rather pools for these plants were assigned an expression value of zero. These artificial zeros, together with any negative expression data obtained by assaying pools were not included in the analysis. Also, note that due to lack of available seed some plants were not analyzed at the bulk seed level even though they had some positive individual seed, and these were excluded from any statistics on bulk seed analysis.

The highest recorded expression level for an individual seed observed with regenerated plants that carried the construct was also noted. This gives an indication of expression potential using the promoter sequence.

Quantification of Aprotinin Reporter Gene Expression in Seed Tissues

Six dry seeds from each ear were individually pulverized and extracted with assay buffer (50 mM phosphate buffered saline pH 7.0, containing 0.05% Tween-20). Single seed samples were placed in extraction tubes held in a rack, with a ball bearing added to each tube, and were then homogenized in a high-speed shaker. Extracts were clarified by centrifugation, and the supernatants recovered and stored on ice prior to analysis. Aprotinin levels were determined using a sandwich-style enzyme-linked immunosorbent assay in which the microtiter plates were coated with rabbit anti-aprotinin anti-serum, the antigen was captured overnight at 4° C., and biotinylated anti-aprotinin antibodies were used to detect the captured antigen. The immune complex was visualized by incubating with alkaline phosphatase conjugated streptavidin and the enzyme substrate p-nitrophenyl phosphate. Samples were assessed at 405 nm using a SpectraMax Plus$^{384}$ plate reader (Molecular Devices; Sunnyvale, Calif.). Assays were performed in triplicate and samples were measured against a bovine aprotinin standard curve. Protein concentrations were determined in duplicate using a dye-binding assay (Bradford, 1976).

Statistical Analysis of Aprotinin Reporter Gene Expression in Transgenic Seeds

Following the six individual seed analysis the mean value for all seed expressing above a background cut off level was determined for each plant. Next, from the mean values for each plant, mean expression levels were determined among all plants derived from a particular independent transformation event and also from all plants derived from the construct. Then, from the mean levels for each transformation event, mean levels were determined among all events derived from the construct. If all seed from a particular plant expressed below the background cut off level, then that plant was scored as zero and was not included in the analysis. However, if all plants from a particular event had been scored as zero, then that event was scored as zero but was included as such in the analysis.

The single seed data was also analyzed focusing on the highest individual seed for each plant. From the highest individual seed values for each plant, mean of high seed expression levels were determined among all plants derived from a particular independent transformation event and also from all plants derived from the construct. Then, from the mean of high seed values for each transformation event, mean levels were determined among all events derived from the construct. If the highest expressing seed from a particular plant expressed below the background cut off level for the assay, then that plant was scored as zero and was not included in the analysis. However, if all plants from a particular event had been scored as zero, then that event was scored as zero but was included as such in the analysis.

The highest recorded expression level for an individual seed observed with regenerated plants that carried the construct was also noted. This gives an indication of expression potential using the promoter sequence.

Analysis of uidA Reporter Gene Expression in Transgenic Plant Tissues $T_1$ seeds were sectioned using a scalpel and were incubated with Jefferson's buffer containing 0.5 mgml$^{-1}$ X-gluc (Jefferson et al., 1987) for up to 3 hours at 37° C. until a clear blue stain was visible. In addition, $T_1$ seeds were allowed to germinate and the resulting $T_1$ seedlings were screened for the presence of pat, and hence for the linked uidA reporter gene, by treating an area of leaf tissue with a 1% glufosinate solution and scoring for resistance to the herbicide. Resistant $T_1$ plants (hemizygous for uidA) were self-pollinated. Representative tissue samples were collected from selected non-seed tissues and were incubated overnight at 37° C. with Jefferson's buffer containing 0.5 mgml$^{-1}$ X-gluc (Jefferson et al., 1987). Blue staining indicated GUS activity. Furthermore, developing $T_2$ seeds were harvested at defined time points and were similarly treated to reveal GUS activity, with sufficient incubation times to reveal any clear staining.

Results

Identification of Maize Globulin-2 as being Highly Expressed in the Developing Embryo The approach taken to identify promoters capable of driving foreign gene expression in maize embryo tissues was to examine relative levels of expression of native maize embryo genes. This was achieved by analyzing clone representation in cDNA libraries prepared from embryo tissues. To enable clones to be identified from various stages of seed development, libraries were prepared from embryo tissues harvested at five time points post-pollination. The selected time points were between 10 and 12 days post-pollination, and at 19, 28, 37 and 46 days post-pollination, the last time point corresponding to fully mature and dried seed. Furthermore, in order to identify clones that would be of value in different corn germplasms, each of the above five embryo pools was made up equally of embryos isolated from each of four lines of maize, comprising a Lancaster line, a Stiff Stalk line, a high protein line and a high oil line.

For each of the five embryo cDNA libraries the DNA sequence of approximately one hundred randomly selected clones was determined. The approximately five hundred cDNA sequences that were so generated were analyzed to reveal the gene expression profile of developing maize embryos and to identify the most highly represented sequences. These sequences were considered to correspond to the most abundant clones or families of clones in the libraries and therefore to the most highly expressed genes or families of genes. Using this approach globulin-2 (Wallace and Kriz, 1991; Genbank accession X53715) was identified as being one of the most highly expressed sequences, with a total of eleven hits out of 530 cloned sequences. This indicates that approximately 2.1% of mRNA molecules present in developing maize embryo tissues encode globulin-2. However, the representation of globulin-2 message varies throughout embryo development. No globulin-2 sequences were identified among approximately one hundred randomly selected clones from the 10 to 12-day post-pollination cDNA library. By contrast, one, five, two and three globulin-2 sequences were identified among a similar number of clones selected from the 19, 28, 37 and 46-day post-pollination cDNA libraries, respectively. Thus, expression of globulin-2 appears to increase later during embryo development, peaking at about 28 days post-pollination.

Confirmation of Globulin-2 as being Highly Expressed in the Developing Maize Embryo Sequence encoding globulin-2 was then confirmed as being highly expressed with a greater level of confidence. A region of the globulin-2 clone was screened for hybridization against a random plating of approximately 80,000 plaques of an equally represented mixture of the five post-pollination embryo cDNA library time points. Thus, a representative pool of plaques corresponding to all four lines of maize and all five time points was assessed. Sequence of a strongly expressed gene should identify a relatively high proportion of plaques, comparable to its representation in the cDNA libraries. Since tens of thousands of plaques were screened there is a greater confidence that the result is representative of all sequences, compared to results obtained using the more restricted DNA sequencing approach described above to initially identify highly expressed clones. This plaque hybridization approach identified approximately 1.4% of the cDNA clones as being globulin-2.

However, a concern with the plaque hybridization approach is that cross hybridization of the selected clone with related but non-identical sequences may result in an overestimation of a particular clone's representation in the libraries. To determine whether this is a serious limitation in the case of globulin-2, the approximate copy number of globulin-2 plus closely related sequences in the maize genome was determined. DNA hybridization analysis using cloned globulin-2 sequence as a probe and genomic DNA prepared from leaf tissue of a standard maize laboratory line as the template identified only three annealing DNA fragments with either of two restriction enzymes used to digest the genomic DNA template. This is consistent with one or at most a few globulin-2 or globulin-2 like sequences being present in the maize genome. Thus, the estimation of globulin-2 clone representation using plaque hybridization data should not be greatly distorted by gene copy number considerations, particularly since some sequences identified by the copy number determination approach may represent pseudogenes that produce no transcripts.

In the Seed Globulin-2 Message is Predominantly Located in Developing Embryo Tissues The tissue and line specificity of expression for globulin-2 was then assessed at the messenger RNA level by conducting a hybridization analysis using globulin-2 cDNA sequence as a probe and RNA prepared from various tissues as the templates. For non-seed material the tissues providing the RNA were pooled samples collected from the four maize lines originally used to make the cDNA libraries. Expression was assessed in leaf, stem, root, tassel, anther, pollen, husk, silk, immature ear and cob tissues. However, in the case of seed tissues expression was assessed in 28-day post-pollination embryos isolated separately from each of the four maize lines used to make the cDNA libraries and in 28-day post-pollination embryos and endosperm tissues isolated from a standard maize laboratory line.

RNA hybridizing to globulin-2 sequence was detected in 28-day post-pollination embryo tissue of all four maize lines used to make the cDNA libraries and of the standard laboratory line. By contrast, globulin-2 message was not detected in endosperm tissue of the standard laboratory line, indicating that within the seed globulin-2 is much more highly expressed in the embryo than the endosperm. RNA hybridizing to globulin-2 sequence was just detectable in stem tissue pooled from the four lines used to make the cDNA libraries, but no globulin-2 message was detected in leaf, root, tassel, anther, pollen, husk, silk, immature ear or cob tissues. Thus, there is a strong seed preference for the expression of globulin-2.

Novel Sequences are Located within the Approximately 3 kb of Sequence 5' and Proximal to the Globulin-2 Open Reading Frame Since expression of globulin-2 was demonstrated to be predominantly in embryo tissue, and it was identified by the library sampling approach deployed here, an extensive genomic clone spanning approximately 3.9 kb of proximal promoter sequence of a globulin-2 gene, but also including the untranslated leader together with approximately 0.24 kb downstream of the translation start codon, was isolated. These sequences were cloned from a library of genomic sequences prepared from leaf tissue of a standard maize laboratory line, using globulin-2 cDNA sequence as a probe. Plaques were thus identified in the genomic library as carrying homologous sequences to globulin-2. Genomic DNA extending approximately 3 kb upstream of the translation start codon for this globulin-2 gene was sub-cloned and the nucleotide sequence determined See FIG. 3 showing the promoter (plus untranslated leader) (SEQ ID NO: 3). The promoter is SEQ ID NO: 4 and is followed by the untranslated leader sequence, which is in bold (SEQ ID NO: 5). By comparison with a previously cloned globulin-2 sequence (Wallace and Kriz, 1991; Genbank accession X53715) and with the here isolated globulin-2 cDNAs, at least the 48 nucleotides of genomic sequence proximal to the translation start codon correspond to the untranslated leader sequence. Comparison of here cloned genomic and cDNA sequences, demonstrates that they show over approximately 98% similarity in the region that they overlap within the globulin-2 open reading frame.

Beyond the predicted globulin-2 leader sequence, more distal to the open reading frame, the here cloned genomic sequence shows a region of extensive similarity to sequences in the Genbank/EMBL databases. This region lies between approximately 1 and 3 kb upstream of the predicted translation start codon and has approximately 88% DNA sequence similarity sequences within an approximately 147 kb maize genomic clone (Genbank accession AF466203). However, this approximately 2 kb block of sequence from the globulin-2 promoter cloned here does not correspond to a contiguous 2 kb region of the AF466203 clone. Rather, approximately 1 kb of the promoter lines up with one region of AF466203, and an adjacent 1 kb of the promoter lines up with a second region of AF466203, separated from the first region by approximately 27 kb. Thus, the overall similarity of the entire globulin-2 promoter with sequence of the AF466203 clone is less than 60%. The regions of AF466203 that show sequence similarity with globulin-2 promoter sequences cloned here are not annotated in Genbank/EMBL as having any functional role. Also, sequence between approximately 2.6 and 3 kb upstream of the predicted globulin-2 translation start codon has approximately 94% DNA sequence similarity with sequence upstream of the maize endosperm b-32 gene, which encodes a putative regulatory factor for zein gene expression (Genbank accession X70153). The globulin-2 and b-32 upstream sequences show sequence similarity on opposite DNA strands and are orientated in opposite directions. Genbank accessions X54212 and AY109436 show lesser degrees of similarity to this same region of the globulin-2 promoter.

The Globulin-2 Promoter Sequence can Drive Transgene Expression in Stably Transformed Seed Tissue To assess the activity and specificity of the globulin-2 promoter sequence a transcription unit was made in which 3 kb of sequence immediately 5' and proximal to the translation start codon of the globulin-2 gene was fused to DNA encoding the uidA reporter gene. The potato protease inhibitor II (PinII) terminator sequence was positioned downstream of the uidA coding sequence. This transcription unit was included in a plant transformation vector. The resulting construct is shown in FIG. 2A.

The promoter-reporter fusion was then stably introduced into the maize genome by *Agrobacterium* mediated transformation. Following the transformation of developing embryo tissues, uidA expression was assessed in non-differentiated callus tissue prior to plant regeneration. GUS activity was detected in callus tissue derived from transformation experiments using the promoter-reporter fusion.

Plants were then regenerated from transformation events obtained using the vector. A total of 194 plants were regenerated from 22 independent transformation events obtained using the globulin-2 promoter-uidA fusion. Seed was harvested, the soluble protein was extracted, and for each plant the level of GUS was determined in each of six randomly selected seeds and also on a pool of 50 randomly selected seeds.

Figure 4:
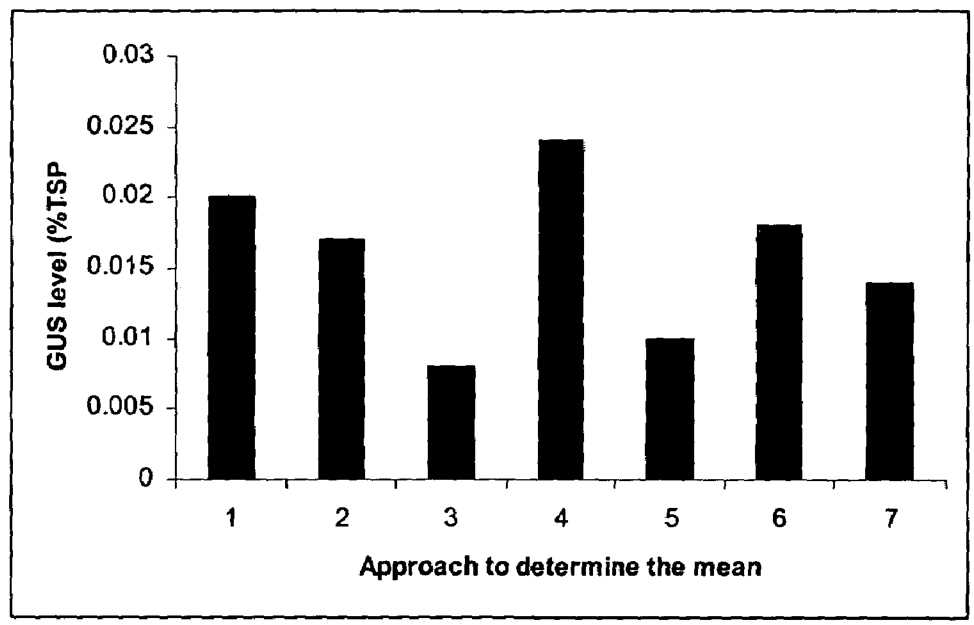
FIG. 4 is a graph summarizing recombinant protein level data derived from single and bulk seed analysis of transgenic maize carrying the globulin-2 promoter/leader-uidA reporter fusion. Data points included to determine mean values (1–7) are as described in the legend to Table 1. The cut off value for detecting expression is 0.006% of total soluble protein (TSP), and non-transgenic control lines never approach this level.

The GUS levels for the transgenic seed are summarized in Table 1 and shown graphically in FIG. 4. The mean GUS level achieved using the globulin-2 promoter was calculated in several alternative ways. Alternative methods of analysis were based on all seeds that had detectable levels of GUS for each plant or only on the seed that had the highest level of GUS for each plant. Also, the mean GUS expression level obtained using the construct was based either on mean expression levels for each independent transformation event, or for each transgenic plant, or on data for each seed. Negative GUS expression data was not included in the analysis. Furthermore, the calculations were either based on individual seed data or on bulk seed data where protein was extracted from a pool of 50 seed. In any bulk sample approximately half the seed are anticipated to be nulls, so that GUS levels calculated from bulk seed analyses are expected to be less than those calculated from single seed analyses.

TABLE 1

Recombinant protein level data derived from single and bulk seed analysis of transgenic maize carrying the globulin-2 promoter-uidA reporter fusion.

| Data included in analysis (see notes) | Sample size | Mean GUS level (% TSP[a]) |
|---|---|---|
| 1 | 168 | 0.020 |
| 2 | 65 | 0.017 |
| 3 | 22 | 0.008 |
| 4 | 65 | 0.024 |
| 5 | 22 | 0.010 |

TABLE 1-continued

Recombinant protein level data derived from single and bulk seed analysis of transgenic maize carrying the globulin-2 promoter-uidA reporter fusion.

| Data included in analysis (see notes) | Sample size | Mean GUS level (% TSP[a]) |
|---|---|---|
| 6 | 34 | 0.018 |
| 7 | 7 | 0.014 |

1: Single seed analysis, where the mean level of GUS for the construct is calculated from all positive seed.
2: Single seed analysis, where the mean level of GUS for the construct is calculated from the mean level of GUS for all plants that do express, itself derived from positive seed data only.
3: Single seed analysis, where the mean level of GUS for the construct is calculated from the mean levels of GUS for each independent transformation event, themselves calculated from the means of GUS for all plants that do express regenerated from each event, which are derived from positive seed data only.
4: Single seed analysis: where the mean level of GUS for the construct is calculated from the highest recorded level of GUS for a seed from each plant that does express.
5: Single seed analysis: where the mean level of GUS for the construct is calculated from the mean levels of GUS for each independent transformation event, themselves calculated from the highest recorded level of GUS for a seed from each plant that does express regenerated from that event.
6: Bulk seed analysis: where the mean level of GUS for the construct is calculated from the level of GUS of each plant that does express.
7: Bulk seed analysis: where the mean level of GUS for the construct is calculated from the mean levels of GUS for each independent transformation event, themselves calculated from the level of GUS of each plant that does express regenerated from that event.
[a]TSP (Total Soluble Protein)

The globulin-2 promoter sequence can clearly drive reporter gene expression in seed. Depending on the method of analysis, mean GUS levels for single T1 seed vary from 0.008% to 0.024% of total soluble protein, whereas mean GUS levels for bulk T1 seed vary from 0.014% to 0.018% of total soluble protein. Also, as a guide to the potential of the globulin-2 promoter sequence to facilitate protein production in plants, the highest level of GUS recorded in a single seed was noted. This highest recorded level of GUS was 0.157% of total soluble protein.

The Maize Globulin-2 Promoter Drives Embryo-preferred Expression

The tissue specificity of expression using the globulin-2 promoter was then assessed. Three of the highest expressing lines for the construct, each from a separate transformation event, were grown in the next generation from $T_1$ seeds and were assessed in a wide range of non-seed tissues. Representative tissue samples were collected from leaves at 21 days post-germination and at 12 days post-pollination. Stem, root and silk tissues were also collected at 12 days post-pollination, and husk and cob tissues at 19 days post-pollination. Also, pollen and anther tissues were collected at the time of pollen shed. All tissue samples were treated to reveal any evidence of GUS activity. The globulin-2 promoter showed no indication of driving GUS activity in any of the above tissues, with the exception of cob tissue, which showed faint localized non-uniform staining. Thus, apart from in cob tissue, the promoter sequence does not drive expression in non-seed tissues, and even in the cob expression is weak.

Expression of the uidA reporter gene was also assessed in $T_1$ seed tissues harvested directly from the $T_0$ transgenic plants. Fully mature dried down seeds were sliced in half and treated to reveal GUS activity. Strong blue staining was observed in the embryo, but no staining was observed in endosperm or aleurone/pericarp tissues. Thus, within the seed, expression appears to be localized to the embryo.

The Maize Globulin-2 Promoter Drives Expression in Embryo Tissues Throughout Development The specificity of globulin-2 promoter was also assessed in seed tissues throughout development. The same plants were utilized as those used to examine non-seed tissue expression, described above. Three of the highest expressing lines, each from a separate transformation event, were grown from $T_1$ seeds. Seed tissues were collected at 12, 19, 27 or 28 and 36 or 37 days post-pollination, the final point corresponding approximately to seed maturity. Seed was then treated to reveal GUS activity. Also, seed tissues were assessed following a dry down period of approximately three weeks. For the 27/28 and 36/37-day post-pollination material and for the dried down material, the seeds were sliced in half prior to the treatment in order to more clearly reveal the pattern of embryo, endosperm and aleurone/pericarp expression. However, for 12 and 19-day post-pollination material, tissue specificity was determined by dissecting out the embryo from the surrounding endosperm prior to the treatment of each tissue type.

The staining pattern indicating GUS activity in seed tissues throughout development is summarized in Table 2.

TABLE 2

Tissue specificity of the globulin-2 promoter-uidA reporter fusions in developing $T_2$ seeds.

| Tissue[a] | GUS staining |
|---|---|
| 12-day embryo | Localized[b] |
| 12-day endosperm | Negative |
| 19-day embryo | Localized |
| 19-day endosperm | Negative |
| 19-day aleurone/pericarp | Negative |
| ~28-day embryo | Localized |
| ~28-day endosperm | Faint |
| ~28-day aleurone/pericarp | Negative |
| ~37-day embryo | Localized |
| ~37-day endosperm | Faint |
| ~37-day aleurone/pericarp | Negative |
| Dried down embryo | Localized |
| Dried down endosperm | Negative |
| Dried down aleurone/pericarp | Negative |

[a]The time points are relative to pollination and the final samples were assessed after approximately 3 weeks dry down.
[b]Two of the three lines examined showed staining.

GUS activity is evident in embryo tissues 12 days after pollination with two of the three lines tested. With the positive lines expression is localized to the apical region of the axial surface of the embryo. At this stage of development no staining is evident in the endosperm. The 19-day post-pollination developing seeds are much larger than the 12-day seeds, and the embryos stained for all three lines. The staining within the embryo is still fairly localized to the apical region of the axial surface. At this stage expression is still not observed in the endosperm or in the aleurone/pericarp for any of the three lines.

By 27/28 days post-pollination the developing seeds have further enlarged, and GUS activity within the embryo is particularly evident in the scutellum. Also, some diffuse, faint GUS activity is evident in the endosperm at 27/28 days post-pollination, although the degree of staining is much fainter in the endosperm than in the embryo. No GUS activity is also observed at this stage in surrounding aleurone/pericarp tissue. The staining pattern in 36/37-day post-pollination embryos is as for that at 27/28 days post-pollination. Given that the seeds do not increase in size during the intervening period, this may reflect a continued unchanging pattern of uidA expression, or a drop off in expression without substantial GUS protein degradation.

Following dry down of seed the pattern of staining in the embryo is very similar to that observed in 27/28-day and 36/37-day post-pollination embryos. Since the dried down tissue is presumably not metabolically active, this staining pattern is taken to reflect the late seed stage GUS activity pattern. No staining was evident in the endosperm or aleurone/pericarp of dried seeds.

Overall, in developing seed tissues GUS activity is strongly embryo preferred, with the scutellum being the site of strongest activity within the embryo. Expression is becoming evident at 12 days post-pollination, and GUS staining is clear right through to the dried down seed stage.

Figure 2B:
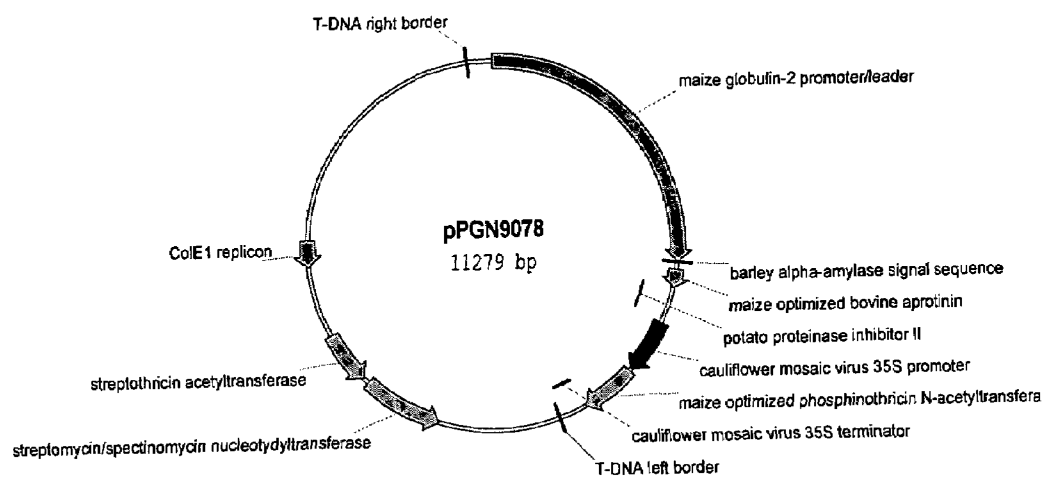

Maize Globulin-2 Promoter Sequences can Drive Expression of a Commercially Important Protein in Stably Transformed Seed Tissue In order to assess whether using the maize globulin-2 promoter would also result in plants expressing a transgene when a second, and in this case commercially important, reporter was utilized, a transcription unit was made in which the globulin-2 promoter was fused to DNA encoding a maize codon optimized version of the *Bos taurus* aprotinin coding sequence. DNA encoding the barley alpha-amylase signal sequence was also included between globulin-2 leader sequence and aprotinin coding sequence. This signal sequence directs the protein product to the cell surface. As for the uidA fusion, the PinII terminator sequence was present downstream of the reporter gene, and the transcription unit was included in a plant transformation vector. The final construct for maize transformation is shown in FIG. 2B.

The promoter-reporter fusion was stably introduced into the maize genome by *Agrobacterium* mediated transformation and plants were regenerated from transformation events obtained using the vector. A total of 72 plants were regenerated from seven independent transformation events obtained using the construct. Seed was harvested, the soluble protein was extracted and for each plant the level of aprotinin was determined in each of six randomly selected seeds.

Figure 5:
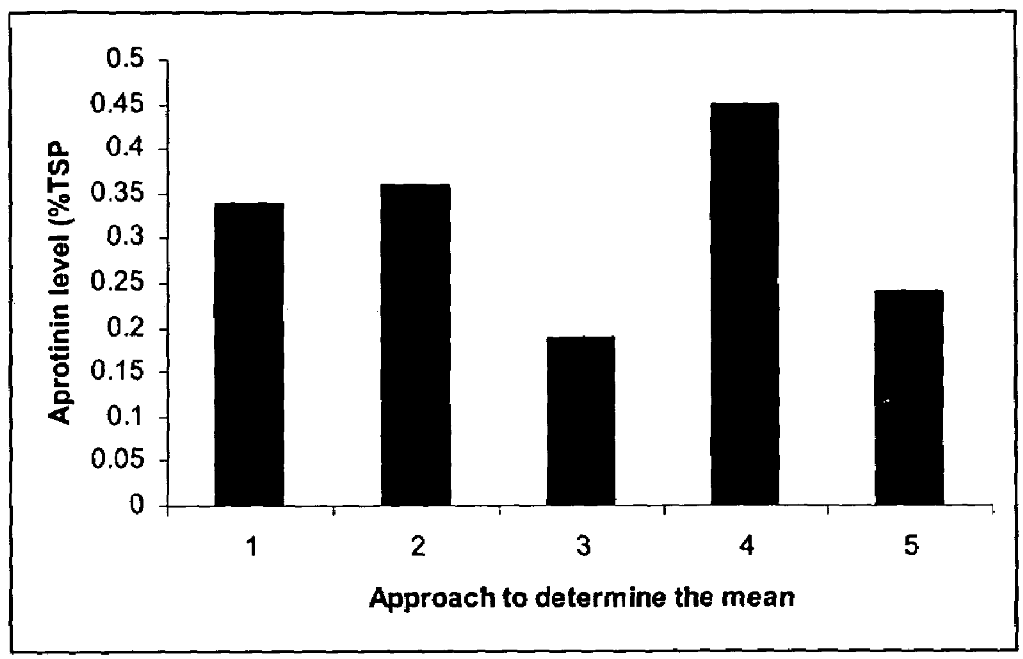
FIG. 5 is a graph summarizing single high seed recombinant protein level data for transgenic maize carrying the globulin-2 promoter-aprotinin reporter fusion. Data points included to determine mean values (1–5) are as described in the legend to Table 3. The cut off value for detecting expression is 0.05% of total soluble protein (TSP), and non-transgenic control lines never approach this level.

The reporter activity data for the transgenic seed are summarized in Table 3 and shown graphically in FIG. 5. The mean aprotinin levels achieved using the globulin-2 promoter were calculated in several alternative ways. Alternative methods of analysis were based on all seeds that had detectable levels of aprotinin for each plant or only on the seed that had the highest level of aprotinin for each plant. Also, the mean aprotinin expression level obtained using the construct was based either on mean expression levels for each independent transformation event, or for each transgenic plant, or on data for each seed. Negative aprotinin expression data was not included in the analysis. The calculations were based on individual seed data.

TABLE 3

Recombinant protein level data derived from single seed analysis of transgenic maize carrying the globulin-2 promoter-aprotinin reporter fusion.

| Data included in analysis (see notes) | Sample size | Mean aprotinin level (% TSP[a]) |
|---|---|---|
| 1 | 81 | 0.34 |
| 2 | 30 | 0.36 |
| 3 | 7 | 0.19 |
| 4 | 30 | 0.45 |
| 5 | 7 | 0.24 |

1: Single seed analysis, where the mean level of aprotinin for the construct is calculated from all positive seed.
2: Single seed analysis, where the mean level of aprotinin for the construct is calculated from the mean level of aprotinin for all plants that do express, itself derived from positive seed data only.
3: Single seed analysis, where the mean level of aprotinin for the construct is calculated from the mean levels of aprotinin for each independent transformation event, themselves calculated from the means of aprotinin for all plants that do express regenerated from each event, which are derived from positive seed data only.
4: Single seed analysis: where the mean level of aprotinin for the construct is calculated from the highest recorded level of aprotinin for a seed from each plant that does express.
5: Single seed analysis: where the mean level of aprotinin for the construct is calculated from the mean levels of aprotinin for each independent transformation event, themselves calculated from the highest recorded level of aprotinin for a seed from each plant that does express regenerated from that event.
[a]TSP (Total Soluble Protein)

The globulin-2 promoter can clearly drive aprotinin expression in maize seed. Depending on the method of analysis, mean aprotinin levels for single T1 seed vary from 0.19% to 0.45% of total soluble protein. Also, as a guide to the potential of the globulin-2 promoter sequence to facilitate commercially important protein production in plants, the highest level of aprotinin recorded in a single seed was noted. This highest recorded level of aprotinin was 3% of total soluble protein.

Discussion

Promoter sequences that are active in plant tissues are vital tools in implementing a range of strategies to engineer plant characteristics. However, overexpression of transgenes throughout the plant can have undesired effects and consequences. Tissue preferred and tissue specific promoters are important for restricting the expression of selected transgenes to particular parts of the plant, thereby eliminating deleterious effects that might arise from constitutive expression. Promoters well suited to expressing transgenes specifically in target tissues are most clearly identified as those that drive the expression of native genes in those tissues. In the case of cereals, including maize, seed tissues are of particular interest for crop improvement and for acting as a repository for protein accumulation. Thus, promoters that are active in seed tissues are of considerable value for crop development and for innovations pertaining to seeds.

The above experiments confirmed globulin-2 message as being one of the most highly prevalent messages in maize embryos by sampling cDNA libraries representing embryo tissues from diverse lines at different stages of development. Globulin-2 sequences were estimated to comprise from 1.4% to 2.1% of the total clones, depending on the method of screening. Furthermore, expression appeared highly preferred for embryo tissues. From a genomic clone extending upstream of the maize globulin-2 translation start codon, approximately 3 kb of globulin-2 promoter sequence was isolated and the nucleotide sequence determined. When fused to the uidA reporter gene and transformed back into maize, this promoter sequence could clearly drive reporter gene acitivity. Also, when fused to a maize codon optimized version of the *Bos taurus* aprotinin reporter gene, the globulin-2 promoter could again drive expression. While the GUS protein was synthesized in the cytoplasm, bovine aprotinin was targeted to the cell surface. Thus, the globulin-2 promoter results in reporter activity whether the reporter protein remains in the cytoplasm or is targeted to the cell surface. Targeting to the cell surface is a strategy that is often used to boost the level of particular proteins in plants (Hood et al., 2003; Streatfield et al., 2003). The globulin-2 promoter can clearly be combined with this cell surface targeting strategy to achieve recombinant protein expression in plants.

The globulin-2 promoter cloned here appears to have a high tissue specificity, with reporter gene expression being seed specific apart from some minor activity in the cob, though even this possibly represents an overflow from seed activity. The globulin-2 promoter can drive embryo expression as early as 12 days after pollination and appears increased by 19 days after pollination, and activity continues throughout embryo development, though with uidA as the reporter gene the presence of GUS activity in late stage embryos may reflect upon previously synthesized protein rather than active transcription and translation. The expression profile observed using the uidA reporter is in line with the observed abundance of cDNAs in the developmental seed libraries, where the native full length globulin-2 promoter appears not to be as active in young developing embryo tissue as in maturing tissue, particularly 28-day post-pollination tissue. During the later stages of seed development promoter activity within the embryo is strongest in the scutellum. However, expression is not observed in the aleurone/pericarp, and only at a very low level in the endosperm from 27 to 37 days post-pollination, but not in the endosperm in dried down seeds.

The strong highly embryo preferred activity of the here cloned maize globulin-2 promoter makes it an excellent choice for seed preferred/specific expression in plants, preferably maize, and other cereals.

REFERENCES

Altschul, S. F., Gish, W., Miller, W., Myers, E. W. and Lipman, D. J. (1990) Basic local alignment search tool. J. Mol. Biol. 215, 403–410.

Altschul, S. F., Madden, T. L., Schaffer, A. A., Zhang, J., Zhang, Z., Miller, W. and Lipman, D. J. (1997) Nucleic Acids Res. 25, 3389–3402.

An, G., Mitra, A., Choi, H. K., Costa, M. A., An, K., Thornburg, R. W. and Ryan, C. A. (1989) Functional analysis of the 3' control region of the potato wound-inducible proteinase inhibitor II gene. Plant Cell 1, 115–122.

Anderson, E. (1944) Sources of effective germplasm in hybrid maize. Annals of the Missouri Botanical Garden 31, 355–361.

Armstrong, C. I. and Green, C. E. (1985) Establishment and maintenance of friable, embryogenic maize callus and involvement of L-proline. Planta 154, 207–214.

Armstrong, C., Green, C. and Phillips, R. (1991) Development and availability of germplasm with high type II culture response. Maize Genet. Coop. News Lett. 65, 92–93.

Ausubel F. M., Brent, R., Kingston, R. E., Moore, D. D., Seidman, J. G., Smith, J. A. and Struhl, K. (Eds.) (1993) Current Protocols in Molecular Biology, John Wiley & Sons, New York.

Bailey, M. R., Woodard, S. L., Callaway, E., Beifuss, K., Magallanes-Lundback, M., Lane, J. R., Horn, M. E., Mallubhotla, H., Delaney, D. D., Ward, M., Van Gastel, F., Howard, J. A. and Hood, E. E. (2004) Improved recovery of active recombinant laccase from maize seed. Appl. Microbiol. Biotechnol. 63, 390–397.

Becker, T. W., Templeman, T. S., Viret, J. F. and Bogorad, L. (1992) The cab-m7 gene: a light-inducible, mesophyll-specific gene of maize. Plant Mol. Biol. 20, 49–60.

Belanger, F. C. and Kriz, A. L. (1991) Molecular basis for allelic polymorphism of the maize globulin-1 gene. Genetics 129, 863–872.

Bradford, M. M. (1976) A rapid and sensitive method for the quantitation of microgram quantities of protein utilizing the principle of protein-dye binding. Anal. Biochem. 72, 248–254.

Brinch-Pedersen, H., Hatzack, F., Sorensen, L. D. and Holm, P. B. (2003) Concerted action of endogenous and heterologous phytase on phytic acid degradation in seed of transgenic wheat (*Triticum aestivum* L.). Transgenic Res. 12, 649–659.

Broglie, R., Coruzzi, G., Fraley, R. T., Rogers, S. G., Horsch, R. B., Niedermeyer, J. G., Fink, C. L. and Chua, N. H. (1984) Light-regulated expression of a pea ribulose-1,5-bisphosphate carboxylase small subunit gene in transformed plant cells. Science 224, 838–843.

Bustos, M. M., Guiltinan, M. J., Jordano, J., Begum, D., Kalkan, F. A. and Hall, T. C. (1989) Regulation of beta-glucuronidase expression in transgenic tobacco plants by an A/T-rich, cis-acting sequence found upstream of a French bean beta-phaseolin gene. Plant Cell 1, 839–853.

Caddick M. X., Greenland, A. J., Jepson, I., Krause, K. P., Qu, N., Riddell, K. V., Salter, M. G., Schuch, W., Sonnewald, U. and Tomsett, A. B. (1998) An ethanol inducible gene switch for plants used to manipulate carbon metabolism. Nat. Biotechnol. 16, 177–180.

Carrillo, C., Wigdorovitz, A., Oliveros, J. C., Zamorano, P. I., Sadir, A. M., Gomez, N., Salinas, J., Escribano, J. M. and Borca, M. V. (1998) Protective immune response to foot-and-mouth disease virus with VP1 expressed in transgenic plants. J. Virol. 72, 1688–1690.

Casas, A. M., Kononowicz, A. K., Zehr, U. B., Tomes, D. T., Axtell, J. D., Butler, L. G., Bressan, R. A. and Hasegawa P. M. (1993) Transgenic sorghum plants via microprojectile bombardment. Proc. Natl. Acad. Sci. USA 90, 11212–11216.

Chatterjee, M., Sparvoli, S., Edmunds, C., Garosi, P., Findlay, K. and Martin, C. (1996) DAG, a gene required for chloroplast differentiation and palisade development in *Antirrhinum majus*. EMBO J. 15, 4194–4207.

Christensen, A. H., Sharrock, R. A. and Quail, P. H. (1992) Maize polyubiquitin genes: structure, thermal perturbation of expression and transcript splicing, and promoter activity following transfer to protoplasts by electroporation. Plant Mol. Biol. 18, 675–689.

Cornejo, M. J., Luth, D., Blankenship, K. M., Anderson, O. D. and Blechl, A. E. (1993) Activity of a maize ubiquitin promoter in transgenic rice. Plant Mol. Biol. 23, 567–581.

Corpet, F. (1988) Multiple sequence alignment with hierarchical clustering. Nucleic Acids Res. 16, 10881–10890.

Coruzzi, G., Broglie, R., Edwards, C. and Chua, N. H. (1984) Tissue-specific and light-regulated expression of a pea nuclear gene encoding the small subunit of ribulose-1,5-bisphosphate carboxylase. EMBO J. 3, 1671–1679.

Creissen, G., Edwards, E. A., Enard, C., Wellburn, A. and Mullineaux, P. (1992) Molecular characterization of glutathione reductase cDNA from pea (*Pisum sativum* L.). Plant J. 2, 129–131.

Crossway, A. (1985) Mol. Gen. Genet. 202, 179–185.

Daniell, H., Streatfield, S. J. and Wycoff, K. (2001) Medical molecular farming: production of antibodies, biopharmaceuticals and edible vaccines in plants. Trends Plant Sci. 6, 219–226.

De Wilde, C., Van Houdt, H., De Buck, S., Angenon, G., De Jaeger, G. and Depicker, A. (2000) Plants as bioreactors for protein production: avoiding the problem of transgene silencing. Plant Mol. Biol. 43, 347–359.

Estruch, J. J., Carozzi, N. B., Desai, N., Duck, N. B., Warren, G. W. and Koziel, M. G. (1997) Transgenic plants: an emerging approach to pest control. Nat. Biotechnol. 15, 137–141.

Feinberg, A. P. and Vogelstein, B. (1983) A technique for radiolabeling DNA restriction endonuclease fragments to high specific activity. Anal. Biochem. 132, 6–13.

Fontes, E. B., Shank, B. B., Wrobel, R. L., Moose, S. P., OBrian, G. R., Wurtzel, E. T. and Boston, R. S. (1991) Characterization of an immunoglobulin binding protein homolog in the maize floury-2 endosperm mutant. Plant Cell 3, 483–496.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA, 80, 4803–4807.

Fromm, M., Taylor, L. P. and Walbot, V. (1985) Expression of genes transferred into monocot and dicot plant cells by electroporation. Proc. Natl. Acad. Sci. USA 82, 5824–5828.

Fromm, M. E., Morrish, F., Armstrong, C., Williams, R., Thomas, J. and Klein, T. M. (1990) Inheritance and expression of chimeric genes in the progeny of transgenic maize plants. Biotechnology (N Y) 8, 833–839.

Geffers, R., Cerff, R. and Hehl, R. (2000) Anaerobiosis-specific interaction of tobacco nuclear factors with cis-regulatory sequences in the maize GapC4 promoter. Plant Mol. Biol. 43, 11–21.

Gordon-Kamm, W., Dilkes, B. P., Lowe, K., Hoerster, G., Sun, X., Ross, M., Church, L., Bunde, C., Farrell, J., Hill, P., Maddock, S., Snyder, J., Sykes, L., Li, Z., Woo, Y. M., Bidney, D. and Larkins, B. A. (1990) Transformation of maize cells and regeneration of fertile transgenic plants. Plant Cell 2, 603–618.

Gould, S. J., Keller, G. A., Hosken, N., Wilkinson, J. and Subramani, S. (1989) A conserved tripeptide sorts proteins to peroxisomes. J. Cell. Biol. 108, 1657–1664.

Grdzelishvili, V. Z., Chapman, S. N., Dawson, W. O. and Lewandowski, D. J. (2000) Mapping of the tobacco mosaic virus movement protein and coat protein subgenomic RNA promoters in vivo. Virology 275, 177–192.

Gruber et al. (1993) Vectors for plant transformation. In: Glick, B. R. and Thompson J. E. (Eds.) Methods in Plant Molecular Biology and Biotechnology, CRC Press, pp. 89–119.

Guilley, H., Dudley, R. K., Jonard, G., Balazs, E. and Richards, K. E. (1982) Transcription of Cauliflower mosaic virus DNA: detection of promoter sequences, and characterization of transcripts. Cell 30, 763–773.

Gurley, W. B., Czarnecka, E., Nagao, R. T. and Key, J. L. (1986) Upstream sequences required for efficient expression of a soybean heat shock gene. Mol. Cell. Biol. 6, 559–565.

Haq, T. A., Mason, H. S., Clements, J. D. and Arntzen, C. J. (1995) Oral immunization with a recombinant bacterial antigen produced in transgenic plants. Science 268, 714–716.

Hiei, Y., Ohta, S., Komari, T. and Kumashiro, T. (1994) Efficient transformation of rice (*Oryza sativs* L.) mediated by *Agrobacterium* and sequence analysis of the boundaries of the T-DNA. Plant J. 6, 271–282.

Higgins, D. G. and Sharp, P. M. (1988) CLUSTAL: a package for performing multiple sequence alignment on a microcomputer. Gene 73, 237–244.

Higgins, D. G. and Sharp, P. M. (1989) Fast and sensitive multiple sequence alignments on a microcomputer. Comput. Appl. Biosci. 5, 151–153.

Hood, E. E., Helmer, G. L., Fraley, R. T. and Chilton, M. D. (1986) The hypervirulence of *Agrobacterium tumefaciens* A281 is encoded in a region of pTiBo542 outside of T-DNA. J. Bacteriol. 168, 1291–1301.

Hood, E. E., Witcher, D. R., Maddock, S., Meyer, T., Baszczynski, C., Bailey, M., Flynn, P., Register, J., Marshall, L., Bond, D., Kulisek, E., Kusnadi, A., Evangelista, R., Nikolov, Z., Wooge, C., Mehigh, R. J., Hernan, R., Kappel, W. K., Ritland, D., Li, C-P. and Howard, J. A. (1997) Commercial production of avidin from transgenic maize: characterization of transformant, production, processing, extraction and purification. Mol. Breed. 3, 291–306.

Hood, E. E., Woodard, S. L. and Horn, M. E. (2002) Monoclonal antibody manufacturing in transgenic plants—myths and realities. Curr. Opin. Biotechnol. 13, 630–635.

Hood, E. E., Bailey, M. R., Beifuss, K., Magallanes-Lundback, M., Horn, M. E., Callaway, E., Drees, C., Delaney, D. E., Clough, R. and Howard, J. A. (2003) Criteria for high-level expression of a fungal laccase gene in transgenic maize. Plant Biotechnol. J. 1, 129–140.

Huang, X., Miller, W., Schwartz, S. and Hardison, R. C. (1992) Parallelization of a local similarity algorithm. Comput. Appl. Biosci. 8, 155–65.

Innis, M., Gelfand, D., Sninsky, J. and White, T. (1990) PCR Protocols: A Guide to Methods and Applications. Academic Press, New York.

Innis, M., Gelfand, D. and Sninsky, J. (1995) PCR Strategies. Academic Press, New York.

Innis, M., Gelfand, D. and Sninsky, J. (1999) PCR Applications: Protocols for Functional Genomics. Academic Press, New York.

Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nat. Biotechnol. 14, 745–750.

Jefferson, R. A., Kavanagh, T. A. and Bevan, M. W. (1987) GUS fusions: beta-glucuronidase as a sensitive and versatile gene fusion marker in higher plants. EMBO J. 6, 3901–7.

Jensen, N. F. (1988) Plant Breeding Methodology. Interscience.

Kalderon, D., Roberts, B. L., Richardson, W. D. and Smith A. E. (1984) A short amino acid sequence able to specify nuclear location. Cell 39, 499–509.

Karlin, S. and Altschul, S. F. (1990) Methods for assessing the statistical significance of molecular sequence features by using general scoring schemes. Proc. Natl. Acad. Sci. USA 87, 2264–2268.

Karlin, S. and Altschul, S. F. (1993) Applications and statistics for multiple high-scoring segments in molecular sequences. Proc. Natl. Acad. Sci. USA 90, 5873–5877.

Klein, T. M., Arentzen, R., Lewis, P. A. and Fitzpatrick-McElligott, S. (1992) Transformation of microbes, plants and animals by particle bombardment. Biotechnology (N Y) 10, 286–291.

Lamphear, B. J., Streatfield, S. J., Jilka, J. M., Brooks, C. A., Barker, D. K., Turner, D. D., Delaney, D. E., Garcia, M., Wiggins, W., Woodard, S. L., Hood, E. E., Tizard, I. R., Lawhorn, B. and Howard, J. A. (2002) Delivery of subunit vaccines in maize seed. J. Control. Release 85, 169–180.

Lee, N., Wang, Y., Yang, J., Ge, K., Huang, S., Tan, J. and Testa, D. (1991) Efficient transformation and regeneration of rice small cell groups. Proc. Nat. Acad. Sci. USA 88, 6389–6393.

Lessard, P. A., Kulaveerasingam, H., York, G. M., Strong, A. and Sinskey, A. J. (2002) Manipulating gene expression for the metabolic engineering of plants. Metab. Eng. 4, 67–79.

Leung, J., Fukuda, H., Wing, D., Schell, J. and Masterson, R. (1991) Functional analysis of cis-elements, auxin response and early developmental profiles of the mannopine synthase bi-directional promoter. Mol. Gen. Genet. 230, 463–474.

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single or double enhancer domains. Transgenic Res. 6, 143–156.

Mason, H. S., Lam, D. M. and Arntzen, C. J. (1992) Expression of hepatitis B surface antigen in transgenic plants. Proc. Natl. Acad. Sci. USA 89, 11745–11749.

Mathur, J. and Koncz, C. (1998) PEG-mediated protoplast transformation with naked DNA. Methods Mol. Biol. 82, 267–276.

Matsuoka, K. and Nakamura, K. (1991) Propeptide of a precursor to a plant vacuolar protein required for vacuolar targeting. Proc. Natl. Acad. Sci. USA 88, 834–838.

Meinkoth, J. and Wahl, G. (1984) Hybridization of nucleic acids immobilized on solid supports. Anal. Biochem. 138, 267–284.

Miki, B. and McHugh, S. (2004) Selectable marker genes in transgenic plants: applications, alternatives and biosafety. J. Biotechnol. 107, 193–232.

Moloney, M. et al. (1989) High efficiency transformation of *Brassica napus* using *Agrobacterium* vectors. Plant Cell Reports 8, 238–242.

Myers, E. W. and Miller, W. (1988) Optimal alignments in linear space. Comput. Appl. Biosci. 4, 11–17.

Needleman, S. B. and Wunsch, C. D. (1970) A general method applicable to the search for similarities in the amino acid sequence of two proteins. J. Mol. Biol. 48, 443–453.

Nessler, C. L. (1994) Metabolic engineering of plant secondary products. Transgenic Res. 3, 109–115.

Neuhausen, S. (1989) A survey of Iowa Stiff Stalk parents derived inbreds and BSSS(HT)C5 using RFLP analysis. MNL 63, 110–111.

Odell, J. T., Nagy, F. and Chua, N. H. (1985) Identification of DNA sequences required for activity of the cauliflower mosaic virus 35S promoter. Nature 313, 810–812.

Oldach, K. H., Becker, D. and Lorz, H. (2001) Heterologous expression of genes mediating enhanced fungal resistance in transgenic wheat. Mol. Plant Microbe Interact. 14, 832–838.

Pearson, W. R. and Lipman, D. J. (1988) Improved tools for biological sequence comparison. Proc. Natl. Acad. Sci. USA 85, 2444–2448.

Pearson, W. R. (1994) Using the FASTA program to search protein and DNA sequence databases. Methods Mol. Biol. 24, 307–331.

Poehlman, J. M. and Sleper, D. A. (1995) Breeding field crops, 4th Edition, Iowa State University Press.

Poirier, Y., Nawrath, C. and Somerville, C. (1995) Production of polyhydroxyalkanoates, a family of biodegradable plastics and elastomers, in bacteria and plants. Biotechnology (N Y) 13, 142–150.

Rogers, J. C. (1985) Two barley alpha-amylase gene families are regulated differently in aleurone cells. J. Biol. Chem. 260, 3731–3738.

Roussell, D. L., Boston, R. S., Goldsbrough, P. B. and Larkins, B. A. (1988) Deletion of DNA sequences flanking an Mr 19,000 zein gene reduces its transcriptional activity in heterologous plant tissues. Mol. Gen. Genet. 211, 202–209.

Russell, D. A. and Fromm, M. E. (1997) Tissue-specific expression in transgenic maize of four endosperm promoters from maize and rice. Transgenic Res. 6, 157–168.

Sambrook, J., Fritsch, E. F. and Maniatis, T. (1989) Molecular Cloning: A Laboratory Manual, 2nd Edition. Cold Spring Harbor Laboratory Press, Plainview, N.Y.

Smith, T. F. and Waterman, M. S. (1981) Adv. Appl. Math. 2, 482–489.

Stacey, J. and Issac, P. G. (1994) Isolation of DNA from plants. Methods Mol. Biol. 28, 9–15.

Sprague, G. F. (1946) Early testing of inbred lines of maize. J. Amer. Soc. Agron. 38, 108–117.

Stiefel, V., Ruiz-Avila, L., Raz, R., Pilar Valles, M., Gomez, J., Pages, M., Martinez-Izquierdo, J. A., Ludevid, M. D., Langdale, J. A., Nelson, T., et al. (1990) Expression of a maize cell wall hydroxyproline-rich glycoprotein gene in early leaf and root vascular differentiation. Plant Cell 2, 785–793.

Streatfield, S. J., Jilka, J. M., Hood, E. E., Turner, D. D., Bailey, M. R., Mayor, J. M., Woodard, S. L., Beifuss, K., Horn, M. E., Delaney, D. E., Tizard, I. R. and Howard, J. A. (2001) Plant-based vaccines: unique advantages. Vaccine 19, 2742–2748.

Streatfield, S. J., Mayor, J. M., Barker, D. K., Brooks, C., Lamphear, B. J., Woodard, S. L., Beifuss, K. K., Vicuna, D. V., Massey, L. A. Massey, Horn, M. E., Delaney, D. D., Nikolov, Z. L., Hood, E. E., Jilka, J. M. and Howard, J. A. (2002) Development of an edible subunit vaccine in corn against enterotoxigenic strains of *Escherichia coli*. In Vitro Cell. Dev. Biol.-Plant 38, 11–17.

Streatfield, S. J., Lane, J. R., Brooks, C. A., Barker, D. K., Poage, M. L., Mayor, J. M., Lamphear, B. J., Drees, C. F., Jilka, J. M., Hood, E. E. and Howard, J. A. (2003) Corn as a production system for human and animal vaccines. Vaccine 21, 812–815.

Takimoto, I., Christensen, A. H., Quail, P. H., Uchimiya, H. and Toki, S. (1994) Non-systemic expression of a stress-response maize polyubiquitin gene (Ubi-1) in transgenic rice plants. Plant Mol. Biol. 26, 1007–1012.

Velten, J. and Schell, J. (1985) Selection-expression plasmid vectors for use in genetic transformation of higher plants. Nucleic Acids Res. 13, 6981–6998.

Vilardell, J., Mundy, J., Stilling, B., Leroux, B., Pla, M., Freyssinet, G. and Pages, M. (1991) Regulation of the maize rab 17 gene promoter in transgenic heterologous systems. Plant Mol. Biol. 17, 985–993.

Wallace, N. H. and Kriz, A. L. (1991) Nucleotide sequence of a cDNA clone corresponding to the maize globulin-2 gene. Plant Physiol. 95, 973–975.

Wan, Y. and Lemaux, P. G. (1994) Generation of large numbers of independently transformed fertile barley plants. Plant Physiol. 104, 37–48.

Waterhouse, P. M., Wang, M. B. and Lough, T. (2001) Gene silencing as an adaptive defense against viruses. Nature 411, 834–842.

Weigel, D. and Nilsson, O. (1995) A developmental switch sufficient for flower initiation in diverse plants. Nature 377, 495–500.

Weising, K., Schell, J. and Kahl, G. (1988) Foreign genes in plants: transfer, structure, expression, and applications. Annu. Rev. Genet. 22, 421–477.

Wohlleben, W., Arnold, W., Broer, I., Hillemann, D., Strauch, E. and Puhler, A. (1988) Nucleotide sequence of the phosphinothricin N-acetyltransferase gene from *Streptomyces virochromogenes* Tu494 and its expression in *Nicotiana tabacum*. Gene 70, 25–37.

Woodard, S. L., Mayor, J. M., Bailey, M. R., Barker, D. K., Love, R. T., Lane, J. R., Delaney, D. E., McComas-Wagner, J. M., Mallubhotla, H. D., Hood, E. E., Dangott, L. J., Tichy, S. E. and Howard, J. A. (2003) Maize-derived bovine trypsin: characterization of the first large-scale, commercial protein product from transgenic plants. Biotechnol. Appl. Biochem. 38, 123–130.

Yang, N. S. and Russell, D. (1990) Maize sucrose synthase-1 promoter drives phloem cell-specific expression of GUS gene in transgenic tobacco plants. Proc. Natl. Acad. Sci. USA 87, 4144–4148.

Ye, X., Al-Babili, S., Kloti, A., Zhang, J., Lucca, P., Beyer, P. and Potrykus, I. (2000) Engineering the provitamin A (beta-carotene) biosynthetic pathway into (carotenoid-free) rice endosperm. Science 287, 303–305.

Yu, H. and Kumar, P. P. (2003) Post-transcriptional gene silencing in plants by RNA. Plant Cell Rep. 22, 167–174.

Zhong, G-Y, Peterson, D., Delaney, D. E., Bailey, M., Witcher, D. R., Register, J. C. (III), Bond, D., Li, C-P., Marshall, L., Kulisek, E., Ritland, D., Meyer, T., Hood, E. E. and Howard, J. A. (1999) Commercial production of aprotinin in transgenic maize seeds. Mol. Breed. 5, 345–356.

What is claimed is:

1. An isolated regulatory element that drives transcription in an embryo-preferred manner, the regulatory element comprising a nucleotide sequence selected from the group consisting of:

a. the nucleotide sequence of SEQ ID NO: 4; and b. A sequence comprising a fragment of the nucleotide sequence set forth in SEQ ID NO: 4.

2. An isolated regulatory element comprising the nucleotide sequence of SEQ ID NO: 4.

3. An isolated regulatory element comprising a fragment of the nucleotide sequence set forth in SEQ ID NO: 4, which is expressed in embryo tissue.

4. An expression cassette comprising a regulatory element that drives transcription in an embryo-preferred manner, the regulatory element comprising a nucleotide sequence selected from the group consisting of:

a. the nucleotide sequence of SEQ ID NO: 4; and b. A sequence comprising a fragment of the nucleotide sequence set forth in SEQ ID NO: 4, which is expressed in embryo tissue.

5. An expression cassette comprising a regulatory element and a nucleotide sequence operably linked to the regulatory element, said regulatory element comprising the nucleotide sequence of SEQ ID NO: 4.

6. An expression cassette comprising a regulatory element and a nucleotide sequence operably linked to the regulatory element, said regulatory element comprising a fragment of the nucleotide sequence of SEQ ID NO: 4 which is expressed in embryo tissue.

7. A transformation vector comprising an expression cassette, the expression cassette comprising a regulatory element selected from the group consisting of:

a. the nucleotide sequence of SEQ ID NO: 4; or b. A sequence comprising a fragment of the nucleotide sequence set forth in SEQ ID NO: 4, which is expressed in embryo tissue.

8. A plant comprising the expression cassette of claim 4.

9. A plant cell comprising the expression cassette of claim 4.

10. An embryo of the plant of claim 8.

11. A method for selectively expressing a nucleotide sequence in a plant embryo, the method comprising transforming a plant cell with a transformation vector comprising an expression cassette, the expression cassette comprising a regulatory element selected from the group consisting of:

(a) the nucleotide sequence of SEQ ID NO:4; and (b) A sequence comprising a fragment of the nucleotide sequence set forth in SEQ ID NO: 4.

* * * * *

SEQUENCE LISTING

```
<160> NUMBER OF SEQ ID NOS: 5

<210> SEQ ID NO 1
<211> LENGTH: 1824
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1

atggtccgtc ctgtagaaac cccaacccgt gaaatcaaaa aactcgacgg cctgtgggca      60

ttcagtctgg atcgcgaaaa ctgtggaatt gatcagcgtt ggtgggaaag cgcgttacaa     120

gaaagccggg caattgctgt gccaggcagt tttaacgatc agttcgccga tgcagatatt     180

cgtaattatg cgggcaacgt ctggtatcag cgcgaagtct ttataccgaa aggttgggca     240

ggccagcgta tcgtgctgcg tttcgatgcg gtcactcatt acggcaaagt gtgggtcaat     300

aatcaggaag tgatggagca tcagggcggc tatacgccat ttgaagccga tgtcacgccg     360

tatgttattg ccgggaaaag tgtacgtatc accgtttgtg tgaacaacga actgaactgg     420

cagactatcc cgccgggaat ggtgattacc gacgaaaacg gcaagaaaaa gcagtcttac     480

ttccatgatt tctttaacta tgccggaatc catcgcagcg taatgctcta caccacgccg     540

aacacctggg tggacgatat caccgtggtg acgcatgtcg cgcaagactg taaccacgcg     600

tctgttgact gccaggtggt ggccaatggt gatgtcagcg ttgaactgcg tgatgcggat     660

caacaggtgg ttgcaactgg acaaggcact agcgggactt tgcaagtggt gaatccgcac     720

ctctgccaac cgggtgaagg ttatctctat gaactgtgcg tcacagccaa aagccagaca     780

gagtgtgata tctacccgct tcgcgtcggc atccggtcag tggcagtgaa gggccaacag     840

ttcctgatta accacaaacc gttctacttt actggctttg gtcgtcatga agatgcggac     900

ttacgtggca aaggattcga taacgtgctg atggtgcacg accacgcatt aatggactgg     960

attggggcca actcctaccg tacctcgcat tacccttacg ctgaagagat gctcgactgg    1020

gcagatgaac atggcatcgt ggtgattgat gaaactgctg ctgtcggctt taacctctct    1080

ttaggcattg gtttcgaagc gggcaacaag ccgaaagaac tgtacagcga agaggcagtc    1140
```

-continued

```
aacggggaaa ctcagcaagc gcacttacag gcgattaaag agctgatagc gcgtgacaaa   1200

aaccacccaa gcgtggtgat gtggagtatt gccaacgaac cggatacccg tccgcaagtg   1260

cacgggaata tttcgccact ggcggaagca acgcgtaaac tcgacccgac gcgtccgatc   1320

acctgcgtca atgtaatgtt ctgcgacgct cacaccgata ccatcagcga tctctttgat   1380

gtgctgtgcc tgaaccgtta ttacggatgg tatgtccaaa gcggcgattt ggaaacggca   1440

gagaaggtac tggaaaaaga acttctggcc tggcaggaga aactgcatca gccgattatc   1500

atcaccgaat acggcgtgga tacgttagcc gggctgcact caatgtacac cgacatgtgg   1560

agtgaagagt atcagtgtgc atggctggat atgtatcacc gcgtctttga tcgcgtcagc   1620

gccgtcgtcg gtgaacaggt atggaatttc gccgattttg cgacctcgca aggcatattg   1680

cgcgttggcg gtaacaagaa agggatcttc actcgcgacc gcaaaccgaa gtcggcggct   1740

tttctgctgc aaaaacgctg gactggcatg aacttcggtg aaaaaccgca gcagggaggc   1800

aaacaacacc atcaccatca ccat                                           1824
```

```
<210> SEQ ID NO 2
<211> LENGTH: 608
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 2

Met Val Arg Pro Val Glu Thr Pro Thr Arg Glu Ile Lys Lys Leu Asp
  1               5                  10                  15

Gly Leu Trp Ala Phe Ser Leu Asp Arg Glu Asn Cys Gly Ile Asp Gln
             20                  25                  30

Arg Trp Trp Glu Ser Ala Leu Gln Glu Ser Arg Ala Ile Ala Val Pro
         35                  40                  45

Gly Ser Phe Asn Asp Gln Phe Ala Asp Ala Asp Ile Arg Asn Tyr Ala
     50                  55                  60

Gly Asn Val Trp Tyr Gln Arg Glu Val Phe Ile Pro Lys Gly Trp Ala
 65                  70                  75                  80

Gly Gln Arg Ile Val Leu Arg Phe Asp Ala Val Thr His Tyr Gly Lys
                 85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Cys Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240
```

```
Leu Cys Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Gln Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Val His Gly Asn Ile Ser Pro Leu Ala Glu Ala Thr Arg
            420                 425                 430

Lys Leu Asp Pro Thr Arg Pro Ile Thr Cys Val Asn Val Met Phe Cys
        435                 440                 445

Asp Ala His Thr Asp Thr Ile Ser Asp Leu Phe Asp Val Leu Cys Leu
    450                 455                 460

Asn Arg Tyr Tyr Gly Trp Tyr Val Gln Ser Gly Asp Leu Glu Thr Ala
465                 470                 475                 480

Glu Lys Val Leu Glu Lys Glu Leu Leu Ala Trp Gln Glu Lys Leu His
                485                 490                 495

Gln Pro Ile Ile Ile Thr Glu Tyr Gly Val Asp Thr Leu Ala Gly Leu
            500                 505                 510

His Ser Met Tyr Thr Asp Met Trp Ser Glu Glu Tyr Gln Cys Ala Trp
        515                 520                 525

Leu Asp Met Tyr His Arg Val Phe Asp Arg Val Ser Ala Val Val Gly
    530                 535                 540

Glu Gln Val Trp Asn Phe Ala Asp Phe Ala Thr Ser Gln Gly Ile Leu
545                 550                 555                 560

Arg Val Gly Gly Asn Lys Lys Gly Ile Phe Thr Arg Asp Arg Lys Pro
                565                 570                 575

Lys Ser Ala Ala Phe Leu Leu Gln Lys Arg Trp Thr Gly Met Asn Phe
            580                 585                 590

Gly Glu Lys Pro Gln Gln Gly Gly Lys Gln His His His His His His
        595                 600                 605

<210> SEQ ID NO 3
<211> LENGTH: 3004
<212> TYPE: DNA
<213> ORGANISM: Zea mays

<400> SEQUENCE: 3

gcgatctgaa gatctggtga acctgagcct gacccatcaa atgtctataa gttttctttg     60
```

-continued

```
tagagaaatt atcggctccc caaatgagtt tccaagcatc atttgtattg gccaccatga    120
tttggcccca agttgcgtct aagtctagaa attgttcata agcttgcacc gacagaggta    180
gctgaaaaat ttcaataagt tgttcctttt ggagagcttc tttgatggta agtttgctgt    240
tgcaagcaaa ggaaaataac tcaggatatt gatgagccgg gatgccccta ttccacatat    300
cttcccagaa aagaatggtt cttccatccc cgatagttgg ggcagccagt cccttgtaat    360
cttggacaag agtaagcaag cttttccacc aaaaggagcc aatttttgag caaccaggta    420
gcctgactgt cctgtaatag ttgctccaaa ccaggttaac ccagggaata tcatgattgt    480
tgaaaaactt gtgcaaaaac ttcagaagca aggctttatt gtgagtctct aatcttacca    540
ctcccaggcc cccatttttt tagtctgtgt aatcatactc caagtagcta gagcaggttt    600
ctttgaattg acgtcgtttc ctctccaaag acagtgtttc cgataagaat caatcttctt    660
taccgtggta accggaattt tcagtgtgca catcaaaaag gtcgggagag ctgagaacac    720
cgagttaaca agctcaagcc tgccagcctg ggagaggagg gcagaggtgc atgataatct    780
cttttgaatc ctatgaatga gcggtaaaaa gtggcagatt ttaggctttg atagaccaag    840
cggaacacca agataggtaa agggcattga acctatctga cagttgaggg ttcctgctag    900
gatcgccatt ttagcaggac tgacattgat ggggtacata cttgatttgt tgtaattcac    960
cttcaacccc gtcgaagttg caaaagagtt cagaacggct ctgagaaaaa atagctgtct   1020
agggcaagct tccattatca gtagtgtgtc atccgcatat tgaactatcg gaaaatcttg   1080
accacaattc tcggccaggg gtaacttgag aaggtcttgc tgccgcgctt tattgatgat   1140
gctctgtaac agatccgccg cgagaacaaa aagaagaggc gagaggggat ctccctgcct   1200
aaccccacgc ttgtagtgaa aggttttccc aggaacacca ttaagaagga ctgatgacgt   1260
gctagaccga agaatatccc taatccagct catccatctg ggcccaaagc ctctatgcaa   1320
cattacctga agaatcaact catgctcaag agaatcaaaa gccttttcaa aatccaattt   1380
gagcacaata atctcttttt ttgaaatatg acaaagatga atatattcaa atgcccaggc   1440
cagacaatcc tgaatggttc tttctttgat gaagccatat tgatttttgt gaacaaggga   1500
agtcatcact gtctgtaacc ggttagccag cagcttagtg atgattttca tactattatt   1560
cagaagcgaa attggtctga aatcgcccac taaactagca ttatccttct tcggaatcag   1620
gacaatataa gaaccattga tgcttcgaag acaaatatcc ccgtggtaaa attggtcaca   1680
taagtcatag aagtcctggg aaataatcgg acaacatttt tttgataaag ttggtattaa   1740
acccatcagg tcccggggat ttatcagaag gaagggacgc cacaatacta tcaatttctt   1800
gctttgaaaa aggctcatct aaccaatgca agtcattgcg gcagagcaac aaactagaaa   1860
gatcaaagac attatccaca aaatcggagg atcccaagcg acatttgaac atattccaaa   1920
gcaggttagt tttgagatca tgctctgtaa agattgagcc actgtcatcc aagagcaacg   1980
caattgtatt acggccatgc cacgcaactg tcatccaaga actttctact cttggattac   2040
acggataaag ttgaagtact acaagcaact ataaacgact agagcctttg cttgagtcct   2100
tttatacgcg gtcgaagagt gtttgcctct ttatttattt gttcagcagg ccccgagaat   2160
cttcaccgct gaagcacacc cgacccgaat aattgataat attgctcaaa tcatatgaga   2220
tggacgctgg ctctgcagct tttagggcct gttcgtttga ctcggaattc atcccggaat   2280
tgttccagct aatcaaatgt tatataaatt agataaccaa tccggctagg aatagttccg   2340
gacggccaat tcctcagaat cgaacgggcc cttagctagt ttcgagtcgt cggaatcagc   2400
```

-continued

```
ttctgctagc taaatgtttt gcttttcata gtctattttt gttagaatcg tttatataaa   2460

aattacatct aaatatagaa tctatcgaat cgtcgtgata gtatgaatgt gatgctgcgc   2520

gtagactcct ttgtcttctt tagcacataa atcgtataaa aattgtcgta acagctattt   2580

tttaagaatc cagattatca gaaatctttg ggaaaaaaag cactctctga aaaagccccg   2640

cgtcgctacg tgcagctcca tctgctccgt gttgtcccca tcccaatcac cgctgtcgct   2700

tcgccgcagg catcccagca gcgagctagc atgcacgcac gcacgcaagc acacggcggc   2760

agctgcacgg atgcggccga gtgcggtagc actgcagcgc gcgcgcgcgc tccacatcgc   2820

cttcgccccg ccacgtacgc ggcccggcct ccacctggcg gcgcgcatgg ctgcgaccct   2880

cgccgcgcca cctcttcata tacgccgcag ctcgcttcga accctcgcat cgaacgcaca   2940

ctcgcactcg cagtcgcacg tacacggtac accacactag ctaccacaga cgacgagcgc   3000

catg                                                                3004
```

```
<210> SEQ ID NO 4
<211> LENGTH: 2953
<212> TYPE: DNA
<213> ORGANISM: Zea mays

<400> SEQUENCE: 4

gcgatctgaa gatctggtga acctgagcct gacccatcaa atgtctataa gttttctttg     60

tagagaaatt atcggctccc caaatgagtt tccaagcatc atttgtattg gccaccatga    120

tttggcccca agttgcgtct aagtctagaa attgttcata agcttgcacc gacagaggta    180

gctgaaaaat ttcaataagt tgttcctttt ggagagcttc tttgatggta agtttgctgt    240

tgcaagcaaa ggaaaataac tcaggatatt gatgagccgg gatgccccta ttccacatat    300

cttcccagaa aagaatggtt cttccatccc cgatagttgg ggcagccagt cccttgtaat    360

cttggacaag agtaagcaag cttttccacc aaaaggagcc aatttttgag caaccaggta    420

gcctgactgt cctgtaatag ttgctccaaa ccaggttaac ccagggaata tcatgattgt    480

tgaaaaactt gtgcaaaaac ttcagaagca aggctttatt gtgagtctct aatcttacca    540

ctcccaggcc cccatttttt tagtctgtgt aatcatactc caagtagcta gagcaggttt    600

ctttgaattg acgtcgtttc ctctccaaag acagtgtttc cgataagaat caatcttctt    660

taccgtggta accggaattt tcagtgtgca catcaaaaag gtcgggagag ctgagaacac    720

cgagttaaca agctcaagcc tgccagcctg ggagaggagg gcagaggtgc atgataatct    780

cttttgaatc ctatgaatga gcggtaaaaa gtggcagatt ttaggctttg atagaccaag    840

cggaacacca agataggtaa agggcattga acctatctga cagttgaggg ttcctgctag    900

gatcgccatt ttagcaggac tgacattgat ggggtacata cttgatttgt tgtaattcac    960

cttcaacccc gtcgaagttg caaaagagtt cagaacggct ctgagaaaaa atagctgtct   1020

agggcaagct tccattatca gtagtgtgtc atccgcatat tgaactatcg gaaaatcttg   1080

accacaattc tcggccaggg gtaacttgag aaggtcttgc tgccgcgctt tattgatgat   1140

gctctgtaac agatccgccg cgagaacaaa aagaagaggc gagaggggat ctccctgcct   1200

aaccccacgc ttgtagtgaa aggttttccc aggaacacca ttaagaagga ctgatgacgt   1260

gctagaccga agaatatccc taatccagct catccatctg ggcccaaagc ctctatgcaa   1320

cattacctga agaatcaact catgctcaag agaatcaaaa gccttttcaa aatccaattt   1380

gagcacaata atctcttttt ttgaaatatg acaaagatga atatattcaa atgcccaggc   1440

cagacaatcc tgaatggttc tttctttgat gaagccatat tgatttttgt gaacaaggga   1500
```

-continued

```
agtcatcact gtctgtaacc ggttagccag cagcttagtg atgattttca tactattatt   1560

cagaagcgaa attggtctga aatcgcccac taaactagca ttatccttct tcggaatcag   1620

gacaatataa gaaccattga tgcttcgaag acaaatatcc ccgtggtaaa attggtcaca   1680

taagtcatag aagtcctggg aaataatcgg acaacatttt tttgataaag ttggtattaa   1740

acccatcagg tcccggggat ttatcagaag gaagggacgc cacaatacta tcaatttctt   1800

gctttgaaaa aggctcatct aaccaatgca agtcattgcg gcagagcaac aaactagaaa   1860

gatcaaagac attatccaca aaatcggagg atcccaagcg acatttgaac atattccaaa   1920

gcaggttagt tttgagatca tgctctgtaa agattgagcc actgtcatcc aagagcaacg   1980

caattgtatt acggccatgc cacgcaactg tcatccaaga actttctact cttggattac   2040

acggataaag ttgaagtact acaagcaact ataaacgact agagcctttg cttgagtcct   2100

tttatacgcg gtcgaagagt gtttgcctct ttatttattt gttcagcagg ccccgagaat   2160

cttcaccgct gaagcacacc cgacccgaat aattgataat attgctcaaa tcatatgaga   2220

tggacgctgg ctctgcagct tttagggcct gttcgtttga ctcggaattc atcccggaat   2280

tgttccagct aatcaaatgt tatataaatt agataaccaa tccggctagg aatagttccg   2340

gacggccaat tcctcagaat cgaacgggcc cttagctagt ttcgagtcgt cggaatcagc   2400

ttctgctagc taaatgtttt gcttttcata gtctattttt gttagaatcg tttatataaa   2460

aattacatct aaatatagaa tctatcgaat cgtcgtgata gtatgaatgt gatgctgcgc   2520

gtagactcct ttgtcttctt tagcacataa atcgtataaa aattgtcgta acagctattt   2580

tttaagaatc cagattatca gaaatctttg ggaaaaaaag cactctctga aaaagccccg   2640

cgtcgctacg tgcagctcca tctgctccgt gttgtcccca tcccaatcac cgctgtcgct   2700

tcgccgcagg catcccagca gcgagctagc atgcacgcac gcacgcaagc acacggcggc   2760

agctgcacgg atgcggccga gtgcggtagc actgcagcgc gcgcgcgcgc tccacatcgc   2820

cttcgccccg ccacgtacgc ggcccggcct ccacctggcg gcgcgcatgg ctgcgaccct   2880

cgccgcgcca cctcttcata tacgccgcag ctcgcttcga accctcgcat cgaacgcaca   2940

ctcgcactcg cag                                                      2953


<210> SEQ ID NO 5
<211> LENGTH: 48
<212> TYPE: DNA
<213> ORGANISM: Zea mays

<400> SEQUENCE: 5

tcgcacgtac acggtacacc acactagcta ccacagacga cgagcgcc                  48
```